United States Patent [19]
Silversides et al.

[11] Patent Number: 5,596,089
[45] Date of Patent: Jan. 21, 1997

[54] OLIGONUCLEOTIDE PROBE AND PRIMERS SPECIFIC TO BOVINE OR PORCINE MALE GENOMIC DNA

[75] Inventors: David W. Silversides, St-Hyacinthe; Isabelle M. Daneau, Drummondville; Alain Houde, Sherbrooke, all of Canada

[73] Assignee: Universite De Montreal, Quebec, Canada

[21] Appl. No.: 196,016

[22] Filed: Feb. 14, 1994

[51] Int. Cl.⁶ .............................. C07H 21/04; C12Q 1/68
[52] U.S. Cl. ........................ 536/24.3; 435/6; 435/91.2; 435/172.3; 435/810; 435/501; 536/23.1; 536/24.1; 536/24.31; 536/24.32; 536/24.33; 935/77; 935/78
[58] Field of Search .................... 435/6, 91.2, 172.3, 435/810; 436/501; 536/23.1, 24.1, 24.3–24.33; 935/77, 78, 88

[56] References Cited

U.S. PATENT DOCUMENTS

| 5,043,272 | 8/1991 | Hartley | 435/91 |
| 5,055,393 | 10/1991 | Kwoh et al. | 435/6 |
| 5,215,884 | 6/1993 | McGraw, III | 435/6 |
| 5,328,827 | 7/1994 | Bishop et al. | 435/6 |

FOREIGN PATENT DOCUMENTS

| 1296770 | 2/1992 | Canada . |
| 1306431 | 8/1992 | Canada . |
| 546762 | 6/1993 | European Pat. Off. . |
| WO90/15155 | 12/1990 | WIPO . |

OTHER PUBLICATIONS

Kageyama et al. (1992) Anim. Sci. Technol, vol. 63, No. 10, abstract only.
Kageyama et al. (1992) Anim. Sci. Technol., vol. 63, No. 10, pp. 1059–1065.
Barany F, 1991, PNAS USA, 88:189–193.
Chomczynski and Sacchi, 1987, Anal. Bicochem., 162:156–159.
Fieck A. et al., 1992, Nucleic Acids Res., 20(17):1785–1791.
Gubbay J et al., 1990, Nature, 346:245–250.
Hopp T. P. and Woods K. R., 1981, PNAS USA, 78:3827–3828.
Kenten J. H. et al., 1991, Clin. Chem., 37(9):1626–1632.
Kirkpatrick B. W. and Monson R. L., 1993, J Reprod. Fertility 98:335–340.
Koopman P. et al., 1991, Nature, 351:117–121.
Kunieda T. et al., 1992, Biology of Reproduction, 46:692–697.
O'Gorman S. et al., 1991, Science, 251:1351–1355.
Orban R. C. et al., 1992, PNAS USA, 89:6861–6865.
Palmiter R. D. et al., 1987, Cell, 50:435–443.
Page et al., 1987, Cell, 51:1091–1104.
Peura T. et al., 1991, Theriogenology, 35(3):547–555.
Saiki, R. K. et al., 1988, Science, 239:487–491.

(List continued on next page.)

Primary Examiner—Stephanie W. Zitomer
Assistant Examiner—Ardin H. Marschel
Attorney, Agent, or Firm—Klauber & Jackson

[57] ABSTRACT

The present invention relates to novel bovine (SEQ ID NO:1) and porcine (SEQ ID NO:2) genomic sequences for the SRY gene along with oligonucleotide primers. The present invention also relates to a method of sexing bovine or porcine tissue by descriminating PCR products obtained by amplification of specific DNA or cDNA sequences of bovine or porcine tissue which is used as a DNA template and wherein two pairs of DNA primers are used for the PCR. The present invention also relates to a method for the genetic manipulation or selection of sexual phenotype in domesticated animals, which comprises using transgenes composed of SRY sequences to cause and control the expression of genetic ablation sequences and genetic switching sequences in undifferentiated and developing gonadal tissues of both XX and XY animals.

2 Claims, 14 Drawing Sheets

```
                                      N-TERMINAL REGION
                  10         20         30         40         50         60
BOVINE    -------MFR VLNDDVYDPA VVQQQTTLAF RKDSSLCTDS HSA-NDQCERG EHVRESSQD
PORCINE   MVQSYASAMF RVLKADDYSP AAQQQNILAL GKGSSLFPTD NHSSNDGRETR GSGRESGQD
HUMAN     M-QSYASAML SVFNSDDYSP AVQENIPALR RSSSFLCTES CNS-KYQCETG ENSKGNVQD
MOUSE     ---------- ---------- ---------- ---------- ---------- ------MEG

HMG (HIGH MOBILITY GROUP) DOMAIN
                  61         70         80         90        100        110        120        130        138
BOVINE    HVKRPMNAFI VWSRERRRKV ALENPKMKNS DISKQLGYEW KRLTDAEKRP FFEEAQRLLA IHRDKYPGYK YRPRRRAK
PORCINE   R                DQ              Q Q   E    W CK   M E                 Q V                KGE
HUMAN     R                DQ   M           R R   E      Q   M E  W   Q  KQ M    E    N              K
MOUSE               M     GE H L QQ        S Q T E        CR  S  E         Q      KI L   E    N    Q H

C-TERMINAL REGION
                 140        150        160        170        180        190        200        210
BOVINE    RP QKSLPADSSI LCNPMHVETL HPFTYRDGCA KTTYSQMESQ LSRSQSVIIT NSLLQKEHHS SWTSLGHNKVT
PORCINE   RA QNLLPAEAAV LCSQVRVEER MYPFTYTVAK AKCSGTESQL SHSQPMNITS SLLQQEDRCN WTGLCTVG*
HUMAN     ML PKNCSLLPAD PASVLCSEVQ LDNRLYRDDC TKATHSRMEH QLGHLPPINA ASSPQQRDRY SHWTKL*
MOUSE     VS QRSGILQPAV ASTKLYNLLQ WDRNPHAITY RQDWSRAAHL YSKNQQSFYW QPVDIPTGHL QQQQQQQQQQ 220        230        240        250        260        270        280
BOVINE    LATRISADFP CNKSLEPGLS CAYFQY*
MOUSE     FHNHHVSQRS GILQPAVAST KLYNLLQWDR NPHAITYRQD WSRAAHLYSK NQQSFYWQPV DIPTGHLQQQ

MOUSE     QQQQQQQQFH NHHQQQQQFY DHHQQQQQQQ QQQQQFHDHH QQKQQFHDHH QQQQQFHDHH HHQEQQFHD    350
          HHQQQQQFHD HQQQQQQQQQ QQFHDHHQQK QQFHDHHHHQ QQQQFHDHQQ QQHQFHDHPQ                 420
          QKQQFHDHPQ QQQQFHDHHH QQQQKQQFHD HHQQKQQFHD HHQQKQQFHD HHQQQQFHDH HHQQQQQQQ      490
          QQQQQFHDQQ LTYLLTADIT GEHTPYQEHL STALWLAVS*                                     529
```

OTHER PUBLICATIONS

Sambrook J., Fritsch E. F. and Maniatis T., 1989, *Molecular Cloning: A laboratory manual*, 2nd ed., Cold Spring Harbour Laboratory Press Sinclair A. G. et al., 1990, Nature, 346:240–244.

Su and Lau, 1993, Am. J. Hum. Genet., 52:24–38.

VanVliet R. A. et al., 1989, Theriogenology, 32(3):421–438.

Whitfield L. S. et al., 1993, Nature, 364:713–715.

Zwigman T. et al., 1993, PNAS USA 90:814–817.

```
                10         20         30         40         50         60
        AAGCTTTTTT TTTTGTTTTG TTCTATTTAG TTTTGATCAT CTGTTAGGTA AAAGTGCAGA
        TTCGAAAAAA AAAACAAAAC AAGATAAATC AAAACTAGTA GACAATCCAT TTTCACGTCT 70         80         90        100        110        120
        AGAGAGTGAT AGATATTACT TCTGCACAGC CTACGCATCT AAGACACCAC ACACCAACCC
        TCTCTCACTA TCTATAATGA AGACGTGTCG GATGCGTAGA TTCTGTGGTG TGTGGTTGGG

F→
               130        140        150        160        170        180
        CCCCCTCCCA CTTTTCCTAC TCCCCAACCG TCAGAACAAA AAAATAAAAA TCAGTCCCTT
        GGGGGAGGGT GAAAAGGATG AGGGGTTGGC AGTCTTGTTT TTTTATTTTT AGTCAGGGAA 190        200        210        220        230        240
        TGAAGTGTTA TATTAACACC AGGGAACTGC TTGGGTACCA AGGTTATGTG TTTTTTCTTT
        ACTTCACAAT ATAATTGTGG TCCCTTGACG AACCCATGGT TCCAATACAC AAAAAAGAAA 250        260        270        280        290        300
        TAATGGAACA GGTTTTTAAT CTAATTTTAG TTGTATCTGA GATTGCCTGT TAAATATGTG
        ATTACCTTGT CCAAAAATTA GATTAAAATC AACATAGACT CTAACGGACA ATTTATACAC 310        320        330        340        350        360
        TTAGTATATA TTAGCATTCT GAAAGTCGTT AGCACAGATA ATAGAATTAC CAGTTATTAG
        AATCATATAT AATCGTAAGA CTTTCAGCAA TCGTGTCTAT TATCTTAATG GTCAATAATC

H→
               370        380        390        400        410        420
        CTACTGGAAT ACGTACATAG ATTTTTCAGC TGCACTTTGA GCCTAAGTGG AGAAGCAGGG
        GATGACCTTA TGCATGTATC TAAAAAGTCG ACGTGAAACT CGGATTCACC TCTTCGTCCC 430        440        450        460        470        480
        TTAGTGATTA GCATGGATTG GGTATCTGTG TATTCAAATA TATAACAGGA TTGGGCTGTT
        AATCACTAAT CGTACCTAAC CCATAGACAC ATAAGTTTAT ATATTGTCCT AACCCGACAA 490        500        510        520        530        540
        TTTCATCTTT TTTTGTTTAA GATAACATTC TCTTACATTC ATAACCGTAG ACAATTTGCT
        AAAGTAGAAA AAAACAAATT CTATTGTAAG AGAATGTAAG TATTGGCATC TGTTAAACGA 550        560        570        580        590        600
        AGTATGTCTG CTGCACCTTC ATCCTTTGAA ATAAGTATAT GAAAATAACT TCATAATGAC
        TCATACAGAC GACGTGGAAG TAGGAAACTT TATTCATATA CTTTTATTGA AGTATTACTG 610        620        630        640        650        660
        ACTTTTTGTA TTTTTAAGCA GGTGTTAGCA CATTCACAAA TTCTGATTAG ATGTAAACAA
        TGAAAAACAT AAAAATTCGT CCACAATCGT GTAAGTGTTT AAGACTAATC TACATTTGTT 670        680        690        700        710        720
        AGAAGAAAGC AGAGCCTTAA TATCCTGTTA AGTAGCTTTG CTTGAGAAAG AGTAGGTTGA
        TCTTCTTTCG TCTCGGAATT ATAGGACAAT TCATCGAAAC GAACTCTTTC TCATCCAACT 730        740        750        760        770        780
        TGGGTTTGGG CTGACTGCCA GGACGTATTG AGGGGAGGTA TTGGGGCGG AGAAATAAAT
        ACCCAAACCC GACTGACGGT CCTGCATAAC TCCCCTCCAT AACCCCGCC TCTTTATTTA 790        800        810        820        830        840
        ATTTCACTGT ATATATTGCA CTAAGTCAGT CTGTGGTAAG AACAACTTAT GAATAGCACC
        TAAAGTGACA TATATAACGT GATTCAGTCA GACACCATTC TTGTTGAATA CTTATCGTGG 850        860        870        880        890        900
        ATAATTTTTA GAACGCTTAC ACCGCATATT ACTTCCTCCC CTTTTAAACA GTGCAGTCGT
        TATTAAAAAT CTTGCGAATG TGGCGTATAA TGAAGGAGGG GAAAATTTGT CACGTCAGCA
```

Fig. 2A

```
          910         920         930         940         950         960
    ATGCTTCTGC  TATGTTCAGA  GTATTGAACG  ACGATGTTTA  CGATCCAGCT  GTGGTACAGC
    TACGAAGACG  ATACAAGTCT  CATAACTTGC  TGCTACAAAT  GCTAGGTCGA  CACCATGTCG

G→                    A→
          970         980         990        1000        1010        1020
    AACAAACTAC  TCTCGCTTTT  AGGAAAGACT  CTTCCTTGTG  CACAGACAGT  CATAGCGCAA
    TTGTTTGATG  AGAGCGAAAA  TCCTTTCTGA  GAAGGAACAC  GTGTCTGTCA  GTATCGCGTT
                       ←7
                       B→
           1030        1040        1050        1060        1070        1080
    ATGATCAGTG  TGAAAGGGGA  GAACATGTTA  GGGAGAGCAG  CCAGGACCAC  GTCAAGCGAC
    TACTAGTCAC  ACTTTCCCCT  CTTGTACAAT  CCCTCTCGTC  GGTCCTGGTG  CAGTTCGCTG
                       ←9

1090        1100        1110        1120        1130        1140
    CCATGAACGC  CTTCATTGTG  TGGTCTCGTG  AACGAAGACG  AAAGGTGGCT  CTAGAGAATC
    GGTACTTGCG  GAAGTAACAC  ACCAGAGCAC  TTGCTTCTGC  TTTCCACCGA  GATCTCTTAG

D→
          1150        1160        1170        1180        1190        1200
    CCAAAATGAA  AAACTCAGAC  ATCAGCAAGC  AGCTGGGATA  TGAGTGGAAA  AGGCTTACAG
    GGTTTTACTT  TTTGAGTCTG  TAGTCGTTCG  TCGACCCTAT  ACTCACCTTT  TCCGAATGTC

F2→
          1210        1220        1230        1240        1250        1260
    ATGCTGAAAA  GCGCCCATTC  TTTGAGGAGG  CACAGAGACT  ACTAGCCATA  CACCGAGACA
    TACGACTTTT  CGCGGGTAAG  AAACTCCTCC  GTGTCTCTGA  TGATCGGTAT  GTGGCTCTGT
                                                       ←6
                                          I→
          1270        1280        1290        1300        1310        1320
    AATACCCGGG  CTATAAATAT  CGACCTCGTC  GGAGAGCCAA  GAGGCCACAG  AAATCGCTTC
    TTATGGGCCC  GATATTTATA  GCTGGAGCAG  CCTCTCGGTT  CTCCGGTGTC  TTTAGCGAAG
                ←5                                                 ←2
    J→                       E→
          1330        1340        1350        1360        1370        1380
    CTGCAGACTC  TTCAATACTA  TGCAACCCGA  TGCATGTAGA  GACATTGCAC  CCCTTCACAT
    GACGTCTGAG  AAGTTATGAT  ACGTTGGGCT  ACGTACATCT  CTGTAACGTG  GGGAAGTGTA
                           ←1

1390        1400        1410        1420        1430        1440
    ACAGGGATGG  TTGTGCCAAG  ACCACATACT  CACAAATGGA  AAGCCAATTA  AGCCGGTCAC
    TGTCCCTACC  AACACGGTTC  TGGTGTATGA  GTGTTTACCT  TTCGGTTAAT  TCGGCCAGTG 1450        1460        1470        1480        1490        1500
    AGTCCGTGAT  CATAACCAAT  TCACTCCTGC  AAAAGGAGCA  TCACAGCAGC  TGGACAAGCC
    TCAGGCACTA  GTATTGGTTA  AGTGAGGACG  TTTTCCTCGT  AGTGTCGTCG  ACCTGTTCGG 1510        1520        1530        1540        1550        1560
    TGGGCCACAA  TAAGGTAACA  TTGGCTACAC  GGATTTCGGC  GGACTTTCCC  TGTAACAAAA
    ACCCGGTGTT  ATTCCATTGT  AACCGATGTG  CCTAAAGCCG  CCTGAAAGGG  ACATTGTTTT
                       ←8
          1570        1580        1590        1600        1610        1620
    GCTTAGAGCC  TGGACTTTCT  TGTGCTTATT  TTCAATATTG  ACTTCCTTAC  TCTCGCTAAC
    CGAATCTCGG  ACCTGAAAGA  ACACGAATAA  AAGTTATAAC  TGAAGGAATG  AGAGCGATTG 1630        1640        1650        1660
    AAAGGCGCTC  TTTATCTCAA  TTTTAAAAAA  AAAAAAAAA A
    TTTCCGCGAG  AAATAGAGTT  AAAATTTTTT  TTTTTTTTT T
```

Fig. 2B

```
                10         20         30         40         50         60
         AAGCTTTTTT TTTTGTTTTG TTCTATTTAG TTTTGATCAT CTGTTAGGTA AAAGTGCAGA
         TTCGAAAAAA AAAACAAAAC AAGATAAATC AAAACTAGTA GACAATCCAT TTTCACGTCT 70         80         90        100        110        120
         AGAGAGTGAT AGATATTACT TCTGCACAGC CTACGCATCT AAGACACCAC ACACCAACCC
         TCTCTCACTA TCTATAATGA AGACGTGTCG GATGCGTAGA TTCTGTGGTG TGTGGTTGGG

F→
               130        140        150        160        170        180
         CCCCCTCCCA CTTTTCCTAC TCCCCAACCG TCAGAACAAA AAAATAAAAA TCAGTCCCTT
         GGGGGAGGGT GAAAAGGATG AGGGGTTGGC AGTCTTGTTT TTTTATTTTT AGTCAGGGAA 190        200        210        220        230        240
         TGAAGTGTTA TATTAACACC AGGGAACTGC TTGGGTACCA AGGTTATGTG TTTTTTCTTT
         ACTTCACAAT ATAATTGTGG TCCCTTGACG AACCCATGGT TCCAATACAC AAAAAAGAAA 250        260        270        280        290        300
         TAATGGAACA GGTTTTTAAT CTAATTTTAG TTGTATCTGA GATTGCCTGT TAAATATGTG
         ATTACCTTGT CCAAAAATTA GATTAAAATC AACATAGACT CTAACGGACA ATTTATACAC 310        320        330        340        350        360
         TTAGTATATA TTAGCATTCT GAAAGTCGTT AGCACAGATA ATAGAATTAC CAGTTATTAG
         AATCATATAT AATCGTAAGA CTTTCAGCAA TCGTGTCTAT TATCTTAATG GTCAATAATC

H→
               370        380        390        400        410        420
         CTACTGGAAT ACGTACATAG ATTTTTCAGC TGCACTTTGA GCCTAAGTGG AGAAGCAGGG
         GATGACCTTA TGCATGTATC TAAAAAGTCG ACGTGAAACT CGGATTCACC TCTTCGTCCC 430        440        450        460        470        480
         TTAGTGATTA GCATGGATTG GGTATCTGTG TATTCAAATA TATAACAGGA TTGGGCTGTT
         AATCACTAAT CGTACCTAAC CCATAGACAC ATAAGTTTAT ATATTGTCCT AACCCGACAA 490        500        510        520        530        540
         TTTCATCTTT TTTTGTTTAA GATAACATTC TCTTACATTC ATAACCGTAG ACAATTTGCT
         AAAGTAGAAA AAAACAAATT CTATTGTAAG AGAATGTAAG TATTGGCATC TGTTAAACGA 550        560        570        580        590        600
         AGTATGTCTG CTGCACCTTC ATCCTTTGAA ATAAGTATAT GAAAATAACT TCATAATGAC
         TCATACAGAC GACGTGGAAG TAGGAAACTT TATTCATATA CTTTTATTGA AGTATTACTG 610        620        630        640        650        660
         ACTTTTTGTA TTTTTAAGCA GGTGTTAGCA CATTCACAAA TTCTGATTAG ATGTAAACAA
         TGAAAAACAT AAAAATTCGT CCACAATCGT GTAAGTGTTT AAGACTAATC TACATTTGTT 670        680        690        700        710        720
         AGAAGAAAGC AGAGCCTTAA TATCCTGTTA AGTAGCTTTG CTTGAGAAAG AGTAGGTTGA
         TCTTCTTTCG TCTCGGAATT ATAGGACAAT TCATCGAAAC GAACTCTTTC TCATCCAACT 730        740        750        760        770        780
         TGGGTTTGGG CTGACTGCCA GGACGTATTG AGGGGAGGTA TTGGGGGCGG AGAAATAAAT
         ACCCAAACCC GACTGACGGT CCTGCATAAC TCCCCTCCAT AACCCCCGCC TCTTTATTTA 790        800        810        820        830        840
         ATTTCACTGT ATATATTGCA CTAAGTCAGT CTGTGGTAAG AACAACTTAT GAATAGCACC
         TAAAGTGACA TATATAACGT GATTCAGTCA GACACCATTC TTGTTGAATA CTTATCGTGG 850        860        870        880        890        900
         ATAATTTTTA GAACGCTTAC ACCGCATATT ACTTCCTCCC CTTTTAAACA GTGCAGTCGT
         TATTAAAAAT CTTGCGAATG TGGCGTATAA TGAAGGAGGG GAAATTTGT CACGTCAGCA
```

Fig. 2C

```
             910        920        930        940        950        960
       ATGCTTCTGC TATGTTCAGA GTATTGAACG ACGATGTTTA CGATCCAGCT GTGGTACAGC
       TACGAAGACG ATACAAGTCT CATAACTTGC TGCTACAAAT GCTAGGTCGA CACCATGTCG

G→                A→
             970        980        990       1000       1010       1020
       AACAAACTAC TCTCGCTTTT AGGAAAGACT CTTCCTTGTG CACAGACAGT CATAGCGCAA
       TTGTTTGATG AGAGCGAAAA TCCTTTCTGA GAAGGAACAC GTGTCTGTCA GTATCGCGTT
                  ←7
                                B→
            1030       1040       1050       1060       1070       1080
       ATGATCAGTG TGAAAGGGGA GAACATGTTA GGGAGAGCAG CCAGGACCAC GTCAAGCGAC
       TACTAGTCAC ACTTTCCCCT CTTGTACAAT CCCTCTCGTC GGTCCTGGTG CAGTTCGCTG
                  ←9

1090       1100       1110       1120       1130       1140
       CCATGAACGC CTTCATTGTG TGGTCTCGTG AACGAAGACG AAAGGTGGCT CTAGAGAATC
       GGTACTTGCG GAAGTAACAC ACCAGAGCAC TTGCTTCTGC TTTCCACCGA GATCTCTTAG

D→
            1150       1160       1170       1180       1190       1200
       CCAAAATGAA AAACTCAGAC ATCAGCAAGC AGCTGGGATA TGAGTGGAAA AGGCTTACAG
       GGTTTTACTT TTTGAGTCTG TAGTCGTTCG TCGACCCTAT ACTCACCTTT TCCGAATGTC

F2→
            1210       1220       1230       1240       1250       1260
       ATGCTGAAAA GCGCCCATTC TTTGAGGAGG CACAGAGACT ACTAGCCATA CACCGAGACA
       TACGACTTTT CGCGGGTAAG AAACTCCTCC GTGTCTCTGA TGATCGGTAT GTGGCTCTGT
                                                                 ←6
                            I→
            1270       1280       1290       1300       1310       1320
       AATACCCGGG CTATAAATAT CGACCTCGTC GGAGAGCCAA GAGGCCACAG AAATCGCTTC
       TTATGGGCCC GATATTTATA GCTGGAGCAG CCTCTCGGTT CTCCGGTGTC TTTAGCGAAG
                  ←5                                                ←2
         J→            E→
            1330       1340       1350       1360       1370       1380
       CTGCAGACTC TTCAATACTA TGCAACCCGA TGCATGTAGA GACATTGCAC CCCTTCACAT
       GACGTCTGAG AAGTTATGAT ACGTTGGGCT ACGTACATCT CTGTAACGTG GGGAAGTGTA
                                                   ←1

1390       1400       1410       1420       1430       1440
       ACAGGGATGG TTGTGCCAAG ACCACATACT CACAAATGGA AAGCCAATTA AGCCGGTCAC
       TGTCCCTACC AACACGGTTC TGGTGTATGA GTGTTTACCT TTCGGTTAAT TCGGCCAGTG 1450       1460       1470       1480       1490       1500
       AGTCCGTGAT CATAACCAAT TCACTCCTGC AAAAGGAGCA TCACAGCAGC TGGACAAGCC
       TCAGGCACTA GTATTGGTTA AGTGAGGACG TTTTCCTCGT AGTGTCGTCG ACCTGTTCGG 1510       1520       1530       1540       1550       1560
       TGGGCCACAA TAAGGTAACA TTGGCTACAC GGATTTCGGC GGACTTTCCC TGTAACAAAA
       ACCCGGTGTT ATTCCATTGT AACCGATGTG CCTAAAGCCG CCTGAAAGGG ACATTGTTTT
                  ←8
            1570       1580       1590       1600       1610       1620
       GCTTAGAGCC TGGACTTTCT TGTGCTTATT TTCAATATTG ACTTCCTTAC TCTCGCTAAC
       CGAATCTCGG ACCTGAAAGA ACACGAATAA AAGTTATAAC TGAAGGAATG AGAGCGATTG 1630       1640       1650       1660
       AAAGGCGCTC TTTATCTCAA TTTTAAAAAA AAAAAAAAA A
       TTTCCGCGAG AAATAGAGTT AAAATTTTTT TTTTTTTTT T
```

Fig. 2D

```
                                    N-TERMINAL REGION
                   10         20         30         40         50         60
BOVINE    ------MFR VLNDDVYDPA VVQQQTTLAF RKDSSLCTDS HSA-NDQCERG EHVRESSQD
PORCINE   MVQSYASAMF RVLKADDYSP AAQQQNILAL GKGSSLFPTD NHSSNDGRETR GSGRESGQD
HUMAN     M-QSYASAML SVFNSDDYSP RSSSFLCTES CNS-KYQCETG ENSKGNVQD
MOUSE     --------- ---------- ---------- ---------- ---------- ----MEG

HMG (HIGH MOBILITY GROUP) DOMAIN
          61         70         80         90        100        110        120        130    138
BOVINE    HVKRPMNAFI VWSRERRRKV ALENPKMKNS DISKQLGYEW KRLTDAEKRP FFEEAQRLLA IHRDKYPGYK YRPRRRAK
PORCINE   R          DQ         QQ         E    W CK M E                Q                    KGE
HUMAN     R          DQ         RR         E    Q  M E                  Q    Q  V            K
MOUSE                GE H L     QQ SQTE    CR      S E               W    KI L   M E N        Q H
                                                                                        E  N

C-TERMINAL REGION
          140        150        160        170        180        190        200        210
BOVINE    RP QKSLPADSSI LCNPMHVETL HPFTYRDGCA KTTYSQMESQ LSRSQSVIIT NSLLQKEHHS SWTSLGHNKVT
PORCINE   RA QNLLPAEAAV LCSQVRVEER MYPFTYTVAK AKCSGTESQL SHSQPMNITS SLLQQEDRCN WTGLCTVG*
HUMAN     ML PKNCSLLPAD PASVLCSEVQ LDNRLYRDDC TKATHSRMEH QLGHLPPINA ASSPQQRDRY SHWTKL*
MOUSE     VS QRSGILQPAV ASTKLYNLLQ WDRNPHAITY RQDWSRAAHL YSKNQQSFYW QPVDIPTGHL QQQQQQQQQ 220        230        240        250        260        270        280
BOVINE    LATRISADFP CNKSLEPGLS CAYFQY*
MOUSE     FHNHHVSQRS GILQPAVAST KLYNLLQWDR NPHAITYRQD WSRAAHLYSK NQQSFYWQPV DIPTGHLQQQ

MOUSE     QQQQQQQQFH NHHQQQQQFY DHHQQQQQQQ QQKQQFHDHH QQQQFHDHH HHHQEQQFHD          350
          HHQQQFHD  HQQQQQQQQ  QFHDHHHHQ  QQQQFHDHQ  QQQFHDHQQ  QHQFHDHPQ           420
          QKQQFHDPQ QQQQFHDHHH QQQKQQFHD  HHQQKQQFHD HHQQKQQFHD HHQQQQFHDH          490
          QQQQFHDQQ LTYLLTADIT GEHTPYQEHL STALWLAVS*                                529
```

Fig. 4

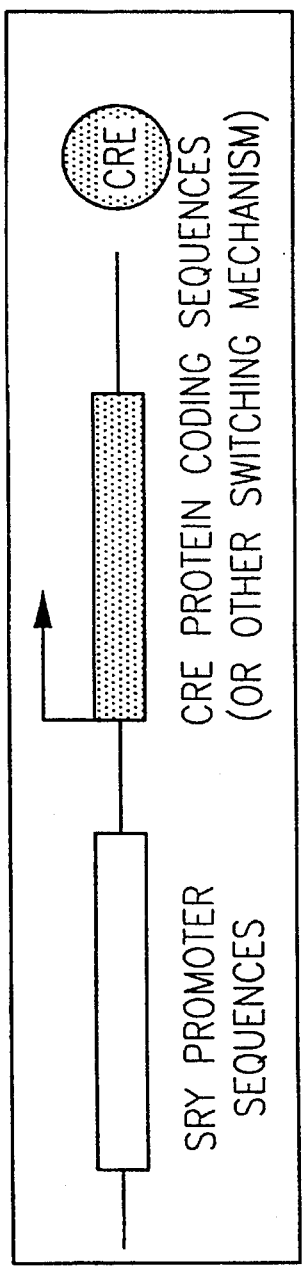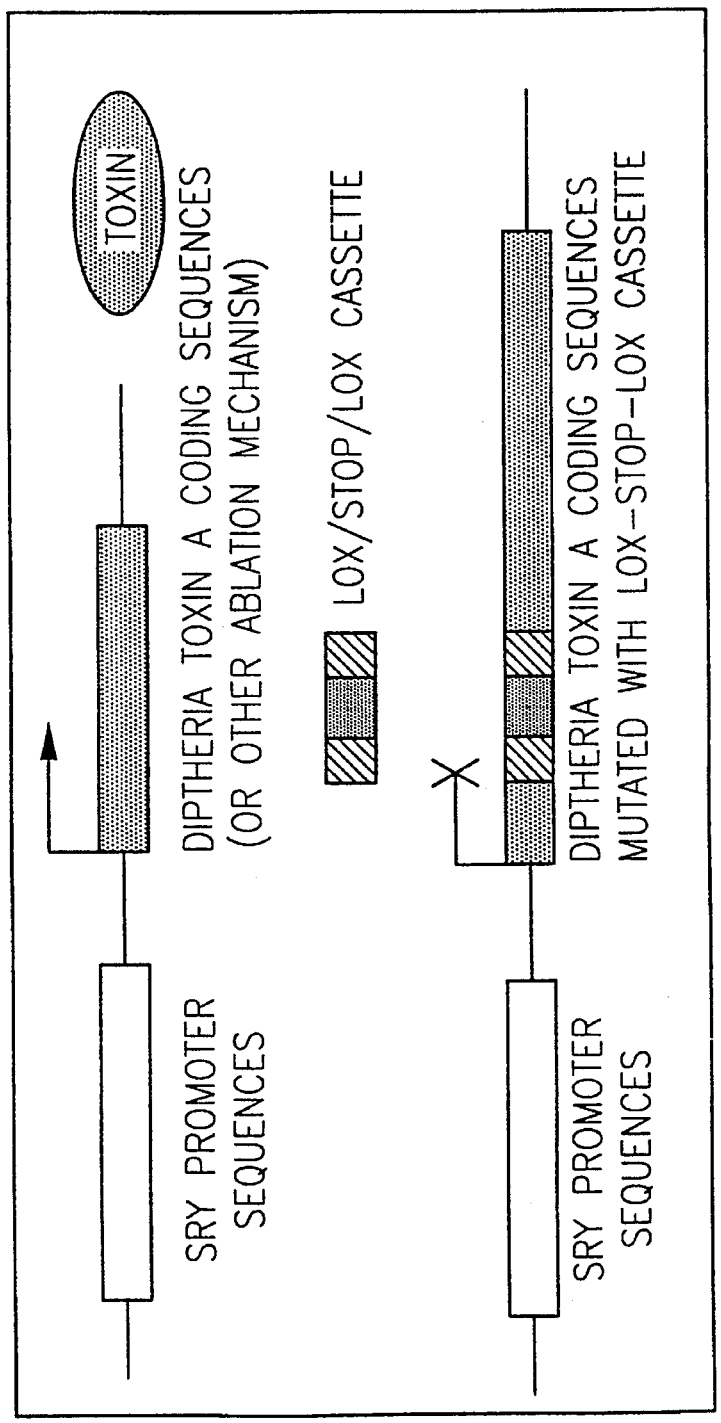
Fig. 9A
Fig. 9B

OLIGONUCLEOTIDE PROBE AND PRIMERS SPECIFIC TO BOVINE OR PORCINE MALE GENOMIC DNA

BACKGROUND OF THE INVENTION (a) Field of the Invention

The invention relates to novel bovine and porcine genomic sequences for the SRY gene, a method for genetic sex determination of bovine or porcine tissue, and a method for the genetic selection of sexual phenotype in domestic animals.

(b) Description of Prior Art

In mammals, males are heterogametic (XY) while females are homogametic (XX), and the male phenotype is correlated with the presence of the Y chromosome. It has been postulated that a control gene, the testes determining factor, is present on the Y chromosome and acts as a developmental switch between the sexes. In the presence of the testes determining factor (i.e. XY), indifferent primitive gonadal tissue develops into testes with a resulting male body phenotype. In the absence of the testes determining factor (i.e. XX), indifferent primitive gonadal tissue fails to receive the testes determining signal, and develops into ovaries with a resulting female body phenotype. The concordance between chromosomal sex and phenotypic sex is not absolute, and the rare exceptions to the rule have been valuable in defining the molecular characteristics of TDF. In 1987, a gene specific to the Y chromosome termed zinc finger on the Y chromosome (ZFY) was isolated and proposed as a candidate gene for the testes determining factor and male sex determination (Page et al., 1987, Cell, 51:1091–1104). Further characterization of ZFY, particularly the facts that a highly homologous gene (ZFX) was found on the X chromosome and that the ZFY gene in marsupials is autosomal, led to the rejection of ZFY as the testes determining factor. In 1990, a new candidate gene for the testes determining factor, named Sex-Determining Region Y or SRY, was described in humans and mice (Sinclair AG et al., 1990, Nature, 346:240–244; Gubbay J et al., 1990, Nature, 346:245–250). When the mouse SRY was introduced into XX mouse embryos via transgenic techniques, phenotypic male mice were generated (Koopman P et al., 1991, Nature, 351:117–121), and it is now generally accepted that SRY is the testes determining factor or genetic switch for the male phenotype in mammals. Structurally the SRY gene contains a centrally located region termed the "High Mobility Group" (HMG) box, which shows reasonably good sequence conservation between species. Interestingly, sequences on either side of the HMG box show a remarkable lack of sequence conservation even between closely related species (Whitfield LS et al., 1993, Nature, 364:713–715). Furthermore the SRY gene is represented uniquely on the Y chromosome, with no X-chromosome homologous sequences. These characteristics make the SRY gene an ideal target for gene based methods of sex determination and sexual phenotype selection.

Manipulation of sex ratios via early determination of sex of embryos is of potential commercial value to the cattle as well as other domesticated animal industries. Several methods have been described for sexing embryos, including X-linked enzyme assays, Y-linked HY antigen assays, cytogenetic assays and Y-linked DNA probes (VanVliet RA et al., 1989, Theriogenology, 32(3):421–438). Reliability, speed and acceptable rates of pregnancy are vital for commercial application of any method of embryo sexing. Recently a novel method for embryo sexing involving the in vitro amplification of Y-chromosome specific repetitive DNA sequences has been described (Peura T et al., 1991, Theriogenology, 35(3):547–555). This method is based on polymerase chain reaction (PCR) amplification technology, an enzymatic method to amplify target fragments of DNA in vitro (Saiki, R. K. et al., 1988, Science, 239:487–491)-Repetitive DNA sequences are repeated sequences of non-coding DNA found scattered throughout the genome. Their function is poorly understood. Repetitive sequences on the Y chromosome can be Y-chromosome specific or they can cross react with repetitive sequences on autosomes. Repetitive sequences can be associated with the Y chromosome but may not necessarily be associated with the male sexual phenotype since they do not code for genes involved with sexual differentiation, and since their highly repetitive nature increases the chances of translocation of sequences to the X chromosome or autosomes. Some Y chromosome repetitive sequences are not Y chromosome specific but are rather Y chromosome enhanced, and are found elsewhere in the genome. More recently, Y-chromosome specific single gene sequences have been used as targets for PCR based sexing regimes, both in lab animals (Kunieda T et al, 1992, Biology of Reproduction, 46:692–697) and domesticated animals (Kirkpatrick B. W. and Monson R. L., 1993., J. Reprod. Fertility, 98:335–340). Domesticated animal single gene targets for PCR based sexing methods have been the Zinc Finger Y chromosome gene, or ZFY (Page et al., 1987, Cell, 51:1091–1104), a gene which is highly conserved between domesticated species and which has an X-chromosome homologous gene, ZFX.

Georges et al. in Patent Cooperation Treaty Application Publication No. 90/15155 on Dec. 13, 1990, disclose a probe specific to Y chromosome based on Y specific repetitive sequences involving about 40 bp and approximately 100,000 copies per genome. This sequence is correlated with the Y chromosome but is not necessarily correlated with male sexual phenotype, due to its highly repetitive nature. This probe is more likely to give false positive results because of its high incidence per genome and thus may not be ideal for the sexing of bovine embryos.

Kwoh D. Y. et al. in U.S. Pat. No. 5,055,393 issued on Oct. 8, 1991, disclose the prenatal sex determination of bovine cells using male-specific oligonucleotides which are repeated male-specific sequences. Again, because these sequences are repeated, false positive results may be expected.

Reed K. et al. in Canadian Patent No. 1,296,770 issued on Feb. 25, 1992, disclose a method for the sex determination in ruminants using bovine repeated sequences on the Y chromosome BRY-1. The main disadvantage of this method is that it is based on repetitive sequence technology and not on gene sequences. Thus, it is not an absolute marker for male sexual determination, nor is it a means for phenotypic manipulation via genetic means.

Ellis S. et al. in Canadian Patent No. 1,306,431 issued on Aug. 18, 1992, disclose nucleic acid probes for prenatal sexing using male-specific repetitive sequences present in a range at about 10 to 5200 copies per genome. This method is not ideal, since it is based on repetitive, non coding sequences specific or enhanced on the Y chromosome.

Kudo T. et al. in European Patent Application Publication No. 546,762 on Jun., 16, 1993, disclose sexing methods for bovine embryos using repetitive sequences, some of which are Y-specific while others are gender non-specific. The main disadvantage of this method is that it is not based on gene sequences, but rather is based on repetitive sequences.

There is nothing in the prior art to indicate that any DNA segments exist in bovine or porcine male DNA which could be used to determine the sex of bovine or porcine tissue with no possibility of false-positive result.

There is nothing in the prior art to suggest that said DNA segments could be useful for in vivo manipulation of sexual phenotype in domestic animals.

It would be highly desirable to be provided with bovine or porcine genomic sequences which would be specific to bull or boar DNA but absent from cow or sow DNA and would not be repeated, repetitive or a so-called satellite DNA.

It would be highly desirable to be provided with a method for the genetic sex determination of bovine or porcine tissue.

It would be highly desirable to be provided with Y chromosome male specific gene sequences including coding sequences, promoter and control sequences useful for the in vivo manipulation of sexual phenotype in domestic animals.

It would be highly desirable to be provided with a method for introducing controllable gene sequences into the genome of domestic animals for the purpose of sexual phenotype, control and selection.

SUMMARY OF THE INVENTION

One aim of the present invention is to provide sequences specific for bull or boar DNA gene sequences but absent from cow or sow DNA which are in fact specific for the Y chromosome and not located in the satellite or repetitive DNA regions.

Another aim of the present invention is to provide bovine or porcine Y chromosome based gene sequences which are not well conserved between species and thus not subject to false positives due to contaminating sequences from other species.

Another aim of the present invention is to provide for novel methods of genetic sex determination of bovine or porcine tissue (including embryos) based on DNA probes derived from the novel bovine and porcine SRY genomic sequences.

Another aim of the present invention is to provide genomic sequences including promoter and control sequences for the SRY gene which may be of use in genetic manipulation of sexual phenotype in domesticated animals.

Another aim of the present invention is to provide for methods for genetic manipulation of sexual phenotypes in domesticated animals.

In accordance with the present invention, there is provided novel bovine (SEQ ID NO:1) and porcine (SEQ ID NO:2) genomic sequences for the SRY gene.

In accordance with the present invention, there is also provided an oligonucleotide primer specifically hybridizing to bovine (SEQ ID NO:1) or porcine (SEQ ID NO:2) male genomic DNA, which comprises substantially the same sequence as that of a DNA sequence selected from the group consisting of:

GCCGCGAGATGGCCATTCTTCCAGGAGGC; (SEQ ID NO:3)

GGGAATTCATGCACAGAGAGAAATACCC; (SEQ ID NO:4)

GGGAATTCAGATCAGCAAGCAGCTGGGA; (SEQ ID NO:5)

ACAGTCATAGCGCAAATGATCAGTG; (SEQ ID NO:6)

GAGAACATGTTAGGGAGAGCAGCCA; (SEQ ID NO:7)

GGGTTGCATAGTATTGAAGAGTCTGC; (SEQ ID NO:8)

GAAGCGATTTCTGTGGCCTCTTGG; (SEQ ID NO:9)

GAATTCAGCCAATGTTACCTTATTGTGGC; (SEQ ID NO:10)

GAATTCAGCTGCTGTGATGCTCT; (SEQ ID NO:11)

TATGCAATCGATGCATGT; (SEQ ID NO:12)

ATAGCCCGGGTATTTGTCTC; (SEQ ID NO:13)

GAATTCTAGTAGTCTCTGTGCCTCC; (SEQ ID NO:14)

GCGAGAGTAGTTGTGC; (SEQ ID NO:15)

CTACTCCCCAACCGTCA; (SEQ ID NO:16)

TCTTCCTTGTGCACAGACAG; (SEQ ID NO:17)

TTATTGTGGCCCAGGCTTGT; (SEQ ID NO:18)

CACACTGATCATTTGCGC; (SEQ ID NO:19)

AGGGTTAGTGATTAGCAT; (SEQ ID NO:20)

AGAAACAAGAATGACGA; (SEQ ID NO:21)

GTTAGCAGAGCCTCCAG; (SEQ ID NO:22)

AAGTCACTCACAGCCCA; (SEQ ID NO:23)

CATGGGTCGCTTGACAC; (SEQ ID NO:24)

GCTATGCTAAGGATTAT; (SEQ ID NO:25)

GACAATTCATAGCTCAAACGATGGAC; (SEQ ID NO:26)

ACTAGAGGAAGTGGTAGAGAGAGTG; (SEQ ID NO:27)

ACTTGGCTGCATAGTACTGCCGCC; and (SEQ ID NO:28)

GGAAGCAAATTCTGTGCCCTCTCTC; (SEQ ID NO:29)

or the complementary strands.

In accordance with the present invention, there is also provided a method of sexing bovine or porcine tissue which comprises the steps of: a) isolating DNA from the bovine or porcine tissue; b) amplifying the isolated DNA of step a) using at least two pairs of DNA primers of the present invention, wherein specific sequences of bovine (SEQ ID NO:1) or porcine (SEQ ID NO:2) male genomic DNA are used as a DNA template; and c) isolating the amplified DNA of step b) and determining the presence or absence of the male genomic DNA sequences in the tissue by direct examination of the amplified products or by hybridization of the amplified product with the DNA segment used as target.

In accordance with the present invention, there is also provided a method for the genetic manipulation or selection of sexual phenotype in domesticated animals, which comprises the steps of: a) creating a transgene construct composed of SRY sequences of bovine (SEQ ID NO:1) or porcine (SEQ ID NO:2) male genomic DNA in an expression vector system; b) transferring the constructs into the genome of both XX and XY animals to cause and control the expression of genetic ablation sequences and genetic switching sequences in the undifferentiated and developing gonadal tissues.

BRIEF DESCRIPTION OF THE DRAWINGS

FIG. 2A and FIG. 2B illustrate the double stranded sequence of bovine SRY 1.7 Kb fragment, composed of a 1.6 Kb genomic HindIII fragment and 3' cDNA sequences;

FIG. 2C and FIG. 2D illustrate the double stranded sequence of porcine SRY 1.7 Kb EcoRI genomic fragment;

FIG. 4 is a comparison of deduced amino acid sequences for the SRY protein between bovine, porcine, human and mouse species;

DETAILED DESCRIPTION OF THE INVENTION

Figure 1A:
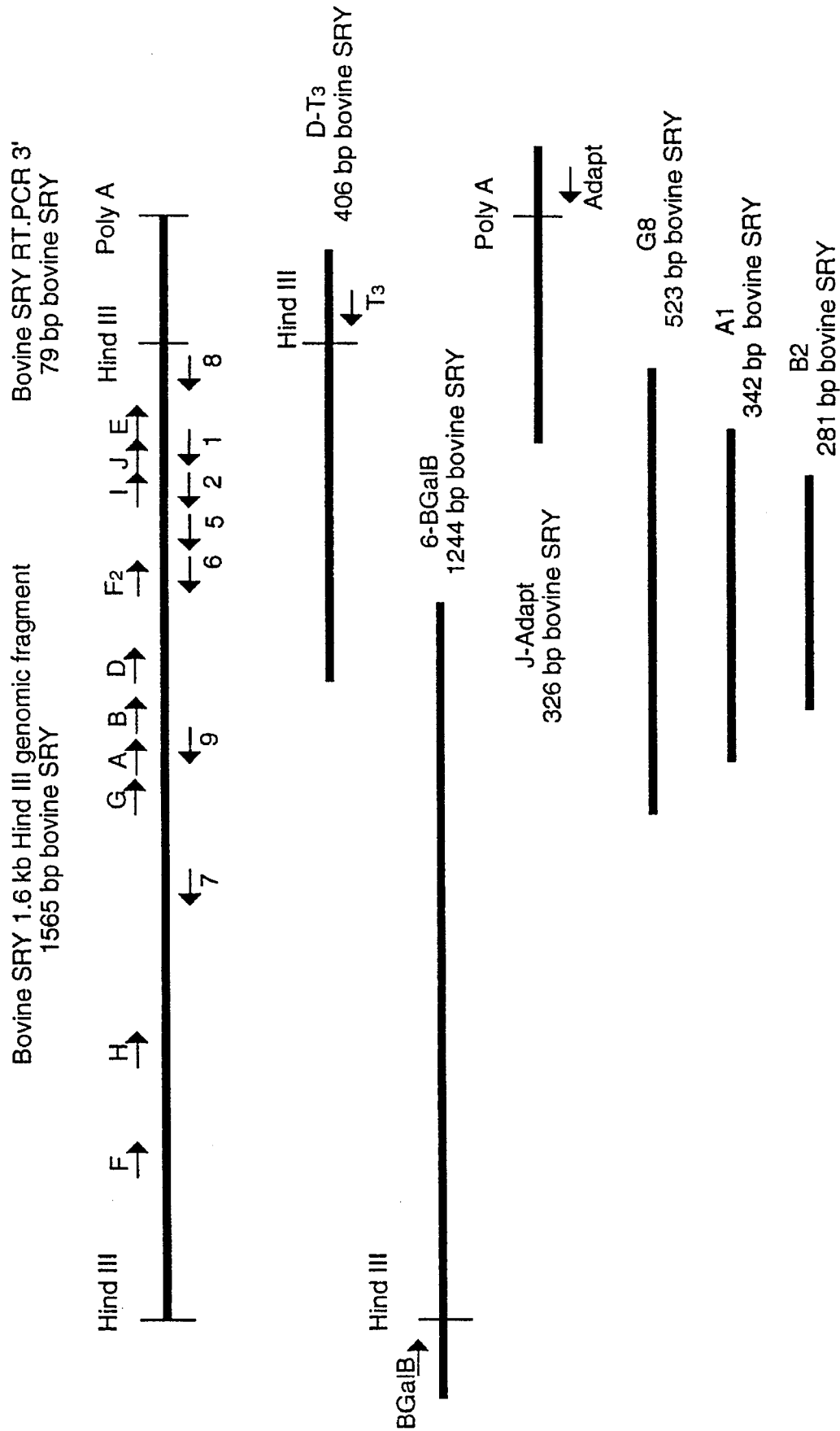
FIG. 1A is a schematic representation of cloning and sequencing strategy for bovine SRY 1.7 Kb fragment, composed of a 1.6 Kb genomic HindIII fragment and 3' cDNA sequences, in accordance with one embodiment of the present invention.

In accordance with the present invention, there is disclosed 1644 bp of novel bovine genomic sequences for the SRY gene, composed of 911 bp of 5' non coding promoter region, an ATG initiation codon, 697 bp of open reading frame (ORF), a TAG stop codon and 45 bp of 3' non coding sequences. By Southern analysis the open reading frame (ORF) sequences are shown to be specific for bull DNA but absent from cow DNA, i.e. are specific for the Y chromosome.

In addition there is disclosed 1667 bp of novel porcine genomic sequences for the SRY gene, composed of 618 bp of 5' non coding promoter region, an ATG initiation codon and 624 bp of open reading frame, a TAA stop codon, and 425 bp of 3' non coding region.

Novel methods of genetic sex determination of bovine or porcine tissue (including embryos) are proposed based on DNA probes derived from bovine SRY genomic sequences; DNA amplification including PCR and the ligase chain reaction (LCR; Barany F, 1991, PNAS USA, 88:189–193); immobilization of probes via biotin-streptavidin-magnetic beads; and detection of probes via fluorescent, chemiluminescent (Kenten J. H. et al., 1991, Clin. Chem., 37(9):1626–1632) and enzymatic means.

Novel methods of in vivo genetic selection of sexual phenotypes are proposed based on DNA sequences derived from bovine and porcine SRY genomic sequences, including coding, promoter and control sequences, and incorporating genetic ablation methods (Palmiter R. D. et al., 1987, Cell, 50:435–443) as well as genetic switching methods (O'Gorman S. et al., 1991, Science, 251:1351–1355; Orban R. C. et al., 1992, PNAS USA, 89:6861–6865).

Size selected genomic mini-library

Genomic DNA was generated from bull white blood cells using standard methods (Sambrook J., Fritsch E. F. and Maniatis T., 1989, *Molecular Cloning: A laboratory manual*, 2nd ed., Cold Spring Harbour Laboratory Press). A restriction digest using HindIII (Pharmacia) was size fractionated on a 0.8% agarose gel, and the bands from 1.3 to 2.0 were physically cut from the gel and purified using glass matrix (Sephaglass™ Bandprep™, Pharmacia) to produce a size selected genomic minilibrary. This bull genomic mini-library presumably contained the putative 1.6 Kb bovine SRY gene sequences described by Sinclair et al. (1990, Nature, 346:240–244). A plasmid vector (Blueskript KS(–), Stratagene) was cut with HindIII and then treated with phosphpatase enzyme (Pharmacia) to prevent subsequent vector religation. The bull genomic mini-library was ligated into the prepared vector using T4 DNA ligase enzyme (Pharmacia) overnight at 16° C. A fraction of the resulting products were then used for an anchored PCR reaction using one primer based on vector sequences and one primer based on homologous regions from human, mouse and rabbit SRY gene sequences (Sinclair A. G. et al., 1990, Nature, 346:240–244; Gubbay J. et al., 1990, Nature, 346:245–250).

TABLE 1

Primers used for PCR amplification and for sequencing
of bovine SRY 1.7 Kb and
porcine 1.7 Kb genomic and cDNA fragments

| | |
|---|---|
| hSRY.F2 | 5'- GCCGCGAGATGGCCATTCTTCCAGGAGGC SEQ ID NO: 3 |
| hSRY.C | 5'- GGGAATTCATGCACAGAGAGAAATACCC SEQ ID NO: 4 |
| hSRY.D | 5'- GGGAATTCAGATCAGCAAGCAGCTGGGA SEQ ID NO: 5 |
| bSRY.A | 5'- ACAGTCATAGCGCAAATGATCAGTG SEQ ID NO: 6 |
| bSRY.B | 5'- GAGAACATGTTAGGGAGAGCAGCCA SEQ ID NO: 7 |
| bSRY.1 | 5'- GGGTTGCATAGTATTGAAGAGTCTGC SEQ ID NO: 8 |
| bSRY.2 | 5'- GAAGCGATTTCTGTGGCCTCTTGG SEQ ID NO: 9 |
| bSRY.3(BT) | 5'- GAATTCAGCCAATGTTACCTTATTGTGGC SEQ ID NO: 10 |
| bSRY.4 | 5'- GAATTCAGCTGCTGTGATGCTCT SEQ ID NO: 11 |
| bSRY.E | 5'- TATGCAATCGATGCATGT SEQ ID NO: 12 |
| bSRY.5(BT) | 5'- ATAGCCCGGGTATTTGTCTC SEQ ID NO: 13 |
| bSRY.6 | 5'- GAATTCTAGTAGTCTCTGTGCCTCC SEQ ID NO: 14 |
| bSRY.7 | 5'- GCGAGAGTAGTTGTGC SEQ ID NO: 15 |
| bSRY.F | 5'- CTACTCCCCAACCGTCA SEQ ID NO: 16 |
| bSRY.G | 5'- TCTTCCTTGTGCACAGACAG SEQ ID NO: 17 |
| bSRY.8 | 5'- TTATTGTGGCCCAGGCTTGT SEQ ID NO: 18 |
| bSRY.9 | 5'- CACACTGATCATTTGCGC SEQ ID NO: 19 |
| bSRY.H | 5'- AGGGTTAGTGATTAGCAT SEQ ID NO: 20 |

TABLE 1-continued

Primers used for PCR amplification and for sequencing
of bovine SRY 1.7 Kb and
porcine 1.7 Kb genomic and cDNA fragments

| | |
|---|---|
| pSRY.A | 5'- AGAAACAAGAATGACGA SEQ ID NO: 21 |
| pSRY.B | 5'- GTTAGCAGAGCCTCCAG SEQ ID NO: 22 |
| pSRY.C | 5'- AAGTCACTCACAGCCCA SEQ ID NO: 23 |
| pSRY.1' | 5'- CATGGGTCGCTTGACAC SEQ ID NO: 24 |
| pSRY.2 | 5'- GCTATGCTAAGGATTAT SEQ ID NO: 25 |
| pHMG.A | 5'- GACAATTCATAGCTCAAACGATGGAC SEQ ID NO: 26 |
| pHMG.B | 5'- ACTAGAGGAAGTGGTAGAGAGAGTG SEQ ID NO: 27 |
| pHMG.1 | 5'- ACTTGGCTGCATAGTACTGCCGCC SEQ ID NO: 28 |
| pHMG.2 | 5'- GGAAGCAAATTCTGTGCCCTCTCTC SEQ ID NO: 29 |
| T(3) | 5'- ATTAACCCTCACTAAAG SEQ ID NO: 30 |
| T(7) | 5'- TAATACGACTCACTATAGGG SEQ ID NO: 31 |
| bGALb | 5'- TGGGTAACGCCAGGGTTTTCCCA SEQ ID NO: 32 |
| dT$_{17}$ADAPT | 5'- GAAGCTTGGATCCGAATTCTTTTTTTTTTTTTTTTT SEQ ID NO: 33 |
| ADAPT | 5'- GAAGCTTGGATCCGAATTC SEQ ID NO: 34 |

In Table 1 above, the engineered 5' EcoRI sites (GAATTC) used for cloning purposes are underlined and BT refers to biotinylation of the 5' nucleotide.

PCR Amplifications, cloning of 3' genomic bovine SRY sequences

An approach of anchored PCR was performed to clone 3' genomic bovine SRY sequences. PCR amplification reactions were prepared as follows: to 100 μl total reaction volume in a 0.5 μl plastic tube, 10 μl of 10× PCR buffer (Cetus), 10 μl of Mg$^{++}$ 15 mM, 2 μl of nonspecific primer (T3 or T7) at a concentration of 20 μM, 1 μl of specific primer (D or C) at a concentration of 20 μM, 2 μl of dNTP (20 mM each of dATP, dCTP, dGTP, dTTP; Pharmacia), 3 μl of ligated plasmid target, 72 μl of water and 50 μl of mineral oil overlay were added. When the reaction mix had attained 80° C., 0.5 μl of TAQ polymerase (Cetus) was added. PCR amplification was performed in an Ericomp™ thermal cycler with conditions as follows: 40 cycles of denaturation (40 sec. at 95° C.), annealing (40 sec. at 55° C.) and elongation (1 min. at 72° C.). Upon completion of the PCR reaction, 30 μl of the reaction mix was fractionated via electrophoresis on a 1.25% agarose gel and visualized using ethidium bromide staining and ultra violet light transillumination. Resulting bands of about 500 bp from D(T3) and D(T7) amplifications were physically excised from the gel, purified with glass beads (Band prep™, Promega), and reamplified via nested PCR using the primers F2(T3), F2(T7), and D(T7). Amplified bands of 450–500 bp were gel purified and ligated into the plasmid vector pGEM(T) (Promega) using T4 DNA ligase (Promega), and then transformed into *E. coli* XL1-Blue bacteria (Stratagene), made competent via the rubidium chloride method (Sambrook J., Fritsch E. F. and Maniatis T., 1989, *Molecular Cloning: A laboratory manual*, 2nd ed., Cold Spring Harbour. Laboratory Press). White bacterial colonies were selected on ampicillin, X-Gal (BRL) and IPTG (BRL) treated agar petri dishes, and mini-prep plasmid DNA prepared via standard methods (Sambrook et al., 1989, idem). Plasmid DNA was restriction digested to confirm inserts of appropriate sizes.

Sequencing

Sequencing was performed using the di-deoxy chain termination method and T7 polymerase (T7 sequencing kit, Pharmacia; Sambrook et al., 1989, idem). Sequencing template was double stranded plasmid DNA purified on a solid phase column matrix (Magic miniprep™, Promega). Initially, plasmid based sequencing primers (SP6, T7) were used. The radionucleotide $^{35}$S dATP (Amersham) was incorporated into the polymerizing chain to aid detection. Sequence reactions were size fractionated via electrophoresis within a 6 or 8% polyacrylamide urea gel. To overcome the inherent misincorporation rate of TAQ polymerase, three independently identified clones were sequenced to obtain a consensus sequence. From preliminary sequence data generated using SP6 and T7 primers, bovine genomic SRY sequences were obtained and used to generate antisense primers for further continued sequencing of 3' bovine SRY genomic sequences and for cloning of the 5' bovine SRY genomic sequences.

5' cloning of bovine SRY sequences

Figure 1B:
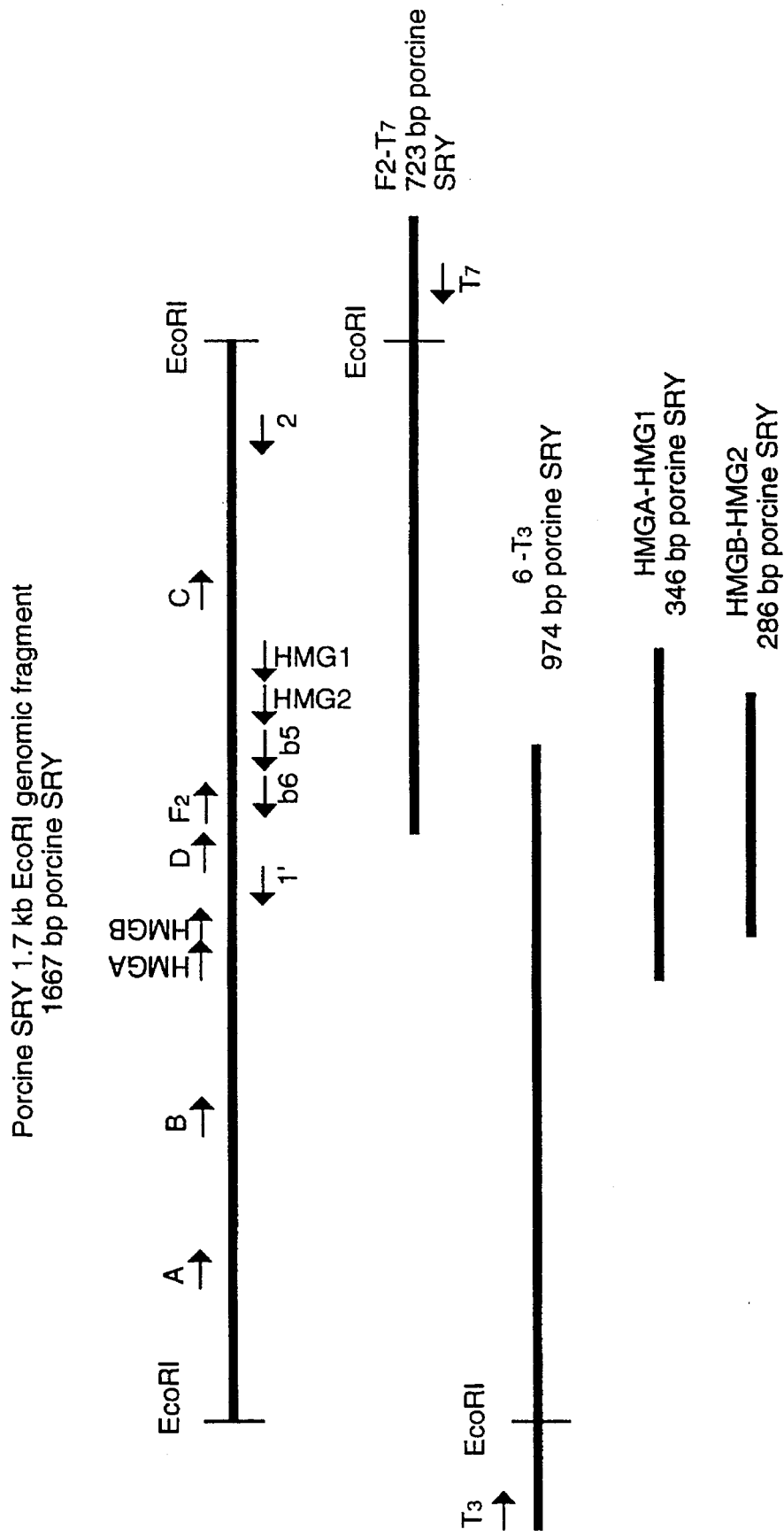
FIG. 1B is a schematic representation of cloning and sequencing strategy for porcine SRY 1.7 Kb EcoRI genomic fragment in accordance with another embodiment of the present invention.

Based on preliminary sequence data generated from the cloned 3' bovine SRY genomic sequences, 5' bovine SRY genomic sequences were generated. Once again a HindIII restricted, 1.3 to 2.0 Kb size selected band of male bovine genomic DNA was ligated into Blueskript vector. Antisense primers bSRY.3(Bt) and bSRY.4 were designed, synthesized and used to amplify via anchored or one sided PCR the 5' end of the bovine SRY genomic sequences. The PCR reaction was similar to the one described above except that annealing was performed at 56° C. and elongation was performed for 2 min. 30 sec. A band of approximately 1.1 Kb was generated using either bSRY.5(Bt) or bSRY.6 and BGalB primers. This band was subcloned into the plasmid pGEM(T) (Promega), insert containing clones were identified, plasmids purified and prepared for sequencing as previously described. A consensus bovine SRY genomic sequence of approximately 1.6 Kb was generated. Cloning and sequencing strategy for bovine SRY 1.6 Kb HindIII genomic fragment is presented in FIG. 1, while primers used for cloning and sequencing are presented in Table 1. HindIII sites are marked in FIG. 1, while relative positions of forward primers G, D, E, F and G as well as reverse primers 5, 6, 7 and 8 are indicated with arrows. Cloned fragments DT3 (representing 406 bp of SRY locus 3' sequences), 6BGalB (representing 1244 bp of bovine SRY locus 5' sequences) and G8 (representing 523 bp of open reading frame from the bovine SRY locus) are also indicated in FIG. 1.

Cloning of 3' cDNA for bovine SRY sequences

Bovine 3' cDNA sequences for the SRY gene were cloned using a strategy of reverse transcription, polymerase chain reaction amplification (RT.PCR). Total adult bull testicular RNA was recovered via the method of Chomczynski and Sacchi (1987, Anal. Biochem., 162:156–159). Poly-A messenger RNA was then derived using oligo-dt bound to magnetized polystyrene beads according to the manufacturer's instructions (Dynabeads™ Oligo (dt)$_{25}$, Dynal Inc.).

One μg of poly-A RNA was reverse transcribed using AMV-reverse transcriptase (Promega), 4 μl of 5× reaction buffer (250 mM Tris-HCl, pH 8.3, 250 mM KCl, 50 mM MgCl$_2$, 2.5 mM spermidine, 50 mM DTT, as supplied by manufacturer), 1 μl dNTP, 0.5μl RNAsin™ (Pharmacia) and 1 μl of the primer dT17 ADAPT (20 μM, see Table 1) were combined in a volume of 20 μl and incubated at 42° C. for 30 min. and at 52° C. for a further 30 min. From this reaction mixture, 1 μl was removed and used as target DNA for a PCR reaction as described previously with the following modifications, 1 μl of primer ADAPT (20 μM) and 1 μl of primer bSRY.I (20 μM) were used in a reaction involving 40 cycles of 40 sec. denaturation at 94° C., 40 sec. annealing at 55° C. and 1 min. 30 sec. elongation at 72° C. From the resulting reaction (total volume of 100 μl), 1 μl was taken as target DNA for a nested PCR amplification using 1 μl of primer ADAPT (20 μM) and 1 μl of primer bSRY.J (20 μM) and a temperature of annealing of 60° C. with the other parameters being those previously described. The PCR reaction was size fractionated on a 1% agarose gel via electrophoresis, and a band larger than 300 bp was identified, cut from the gel, purified and ligated into the plasmid vector pGEM(t) (Promega). After reintroduction of these ligated plasmids into *E. coli* XL1-Blue™ bacteria (Stratagene), mini-prep plasmid DNA was prepared and restriction digested with EcoRI, and insert containing plasmids were thus identified. Three independent positive plasmids were. prepared for sequencing, which was performed as previously described.

Southern analysis

To verify the specificity of the described bovine SRY genomic sequences for bull DNA, a southern blot analysis was performed using cow and bull genomic DNA. Based on homologous regions between bovine, human and mouse sequences, a fragment of 523 bp specified by primers bSRY.G and bSRY.8 was amplified via PCR from genomic bull DNA, gel purified and labelled using digoxigenin incorporated nucleotides and Klenow polymerase as per manufactures' instructions (DIG DNA Labelling and Detection Kit™, Boehringer Mannheim; The DIG System user's guide for filter hybridization, Boehringer Mannheim 1993). Genomic DNA was generated via blood leukocyte extraction from three cows and four bulls using standard extraction techniques (Sambrook et al., 1989, idem). Ten μg of genomic DNA were digested with HindIII (Pharmacia) restriction enzyme and size fractionated via electrophoresis on a 0.8% agarose gel. The genomic DNA digest was then transferred to a neutral nylon membrane (Hybond-N™, Amersham) via capillarity using 20×SSC buffer (3M NaCl, 75 mM Na Citrate pH 7.0). Membranes were prehybridized for 4 hours and hybridized overnight in the presence of the digoxigenin incorporated bSRY.G8 probe. Specific signals were then detected with a chemiluminescent detection system as per manufacturers instructions (The DIG System User's Guide for Filter Hybridization, Boehringer Mannheim 1993), and exposure of the membrane to radiographic film (XAR2™, Kodak) for 6 hours.

PCR analysis and detection of bovine SRY sequences

To further verify the specificity of the described SRY genomic sequences for bull DNA, a PCR amplification analysis was performed using cow and bull genomic DNA. Primer pairs on either side of the HMG box were designed and synthesized to provide amplified bands as follows:

G8=523 bp, Al=342 bp, B2=281 bp.

Cow and bull genomic DNA were isolated from blood leukocytes using standard methods (Sambrook et al., 1989, idem). PCR amplification were performed as previously described with the following modifications, 0.5 μg of genomic DNA was used as target; 1 μl each of specific primer (20 μm) were used, and cycling of 40 sec. at 94° C., 40 sec. at 60° C. and 45 sec. at 72° C. was performed 45 times. To visualize the results, 30 μl of reaction was size fractionated via electrophoresis through a 2.0% agarose gel.

Cloning of porcine SRY sequences

Figure 7:
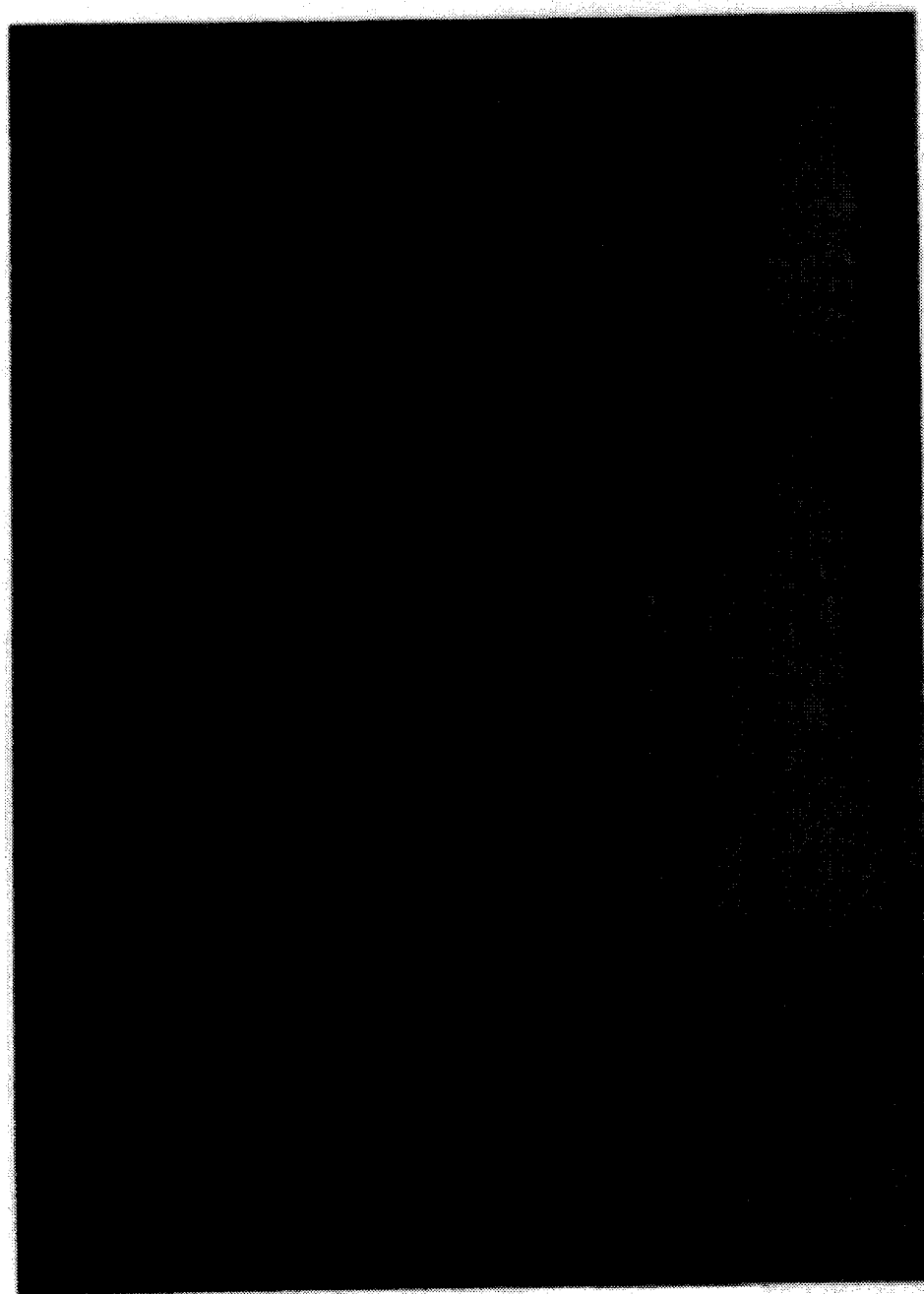
FIG. 7 is a southern analysis of porcine male genomic DNA restricted with a panel of enzymes.

Based on the Southern results described in FIG. 7, which depict a band of approximately 1.7 Kb when porcine male genomic DNA is restricted with EcoRI and probed with bovine SRY G8 fragment, the porcine SRY genomic sequences were amplified by PCR and cloned. The cloning strategy is presented in FIG. 1B, while the completed sequences are presented in FIG. 2B. As in the case of bovine SRY sequences, an approach of anchored PCR amplification of size selected genomic fragments ligated into bacterial plasmid vectors was used. A size selected mini-library of porcine male genomic DNA was generated by ligating EcoRI restriction fragments of approximately 1.7 Kb into the bacterial plasmid Blueskript KS(−) (Stratagene). To clone porcine SRY 3' sequences, a primary amplification using primer hSRY.D (Table 1) with primer T(3) or T(7) was performed on the mini-library. This was followed by a nested amplification using primer hSRY.F2 and T(7), to give an amplified DNA band of 723 bp designated pSRY F2.T7, which was cloned into the bacterial vector pGEM(t) (Promega) as described previously. To clone porcine SRY 5' sequences, a primary amplification using primer bSRY.5(Bt) and primer T(3) or T(7) was performed on the mini-library- This was followed by a nested amplification using primer bSRY.6 and T(3), to give an amplified DNA band of 974 bp designated pSRY 6.T3, which was again cloned into the bacterial vector pGEM(t) (Promega). Plasmid were introduced into *E. coli* XL1-Blue bacteria as described, and positive colonies identified by plasmid mini-prep digestion with EcoRI. Sequencing was performed as described for bovine SRY sequences.

RESULTS

Figure 3A:
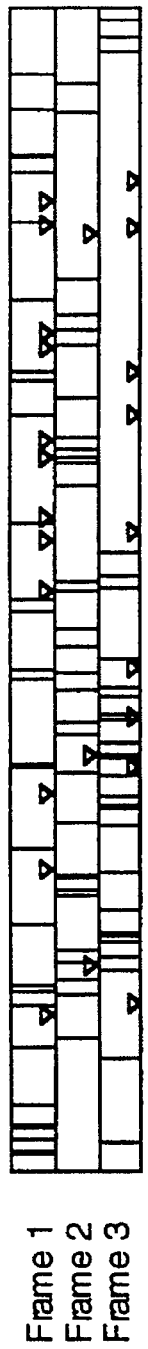
FIG. 3A is the analysis of open reading frames for the bovine SRY 1.7 Kb HindIII genomic fragment.
Figure 3B:
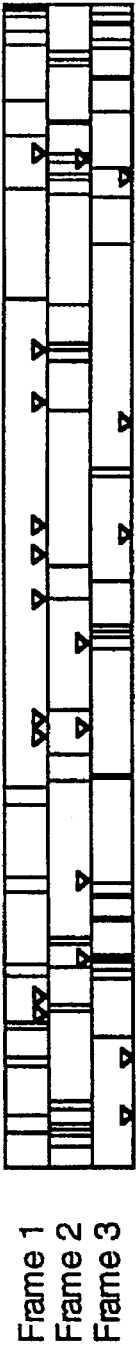
FIG. 3B is the analysis of open reading frames for the porcine SRY 1.7 Kb EcoRI genomic fragment.
Figure 5A:
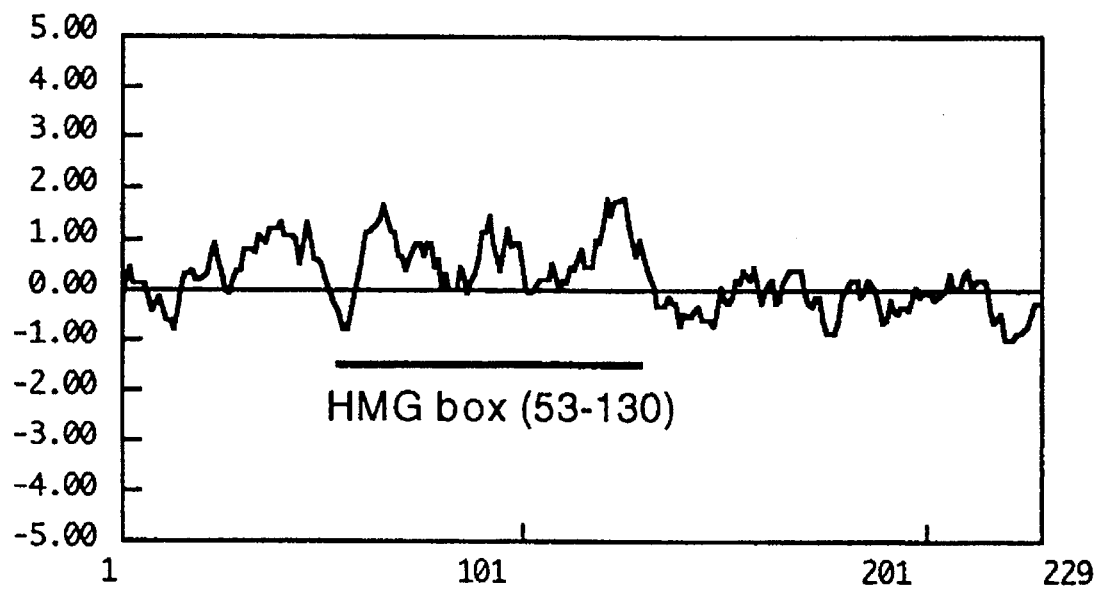
FIG. 5A is the hydropathy profile of bovine SRY open reading frame.
Figure 5B:
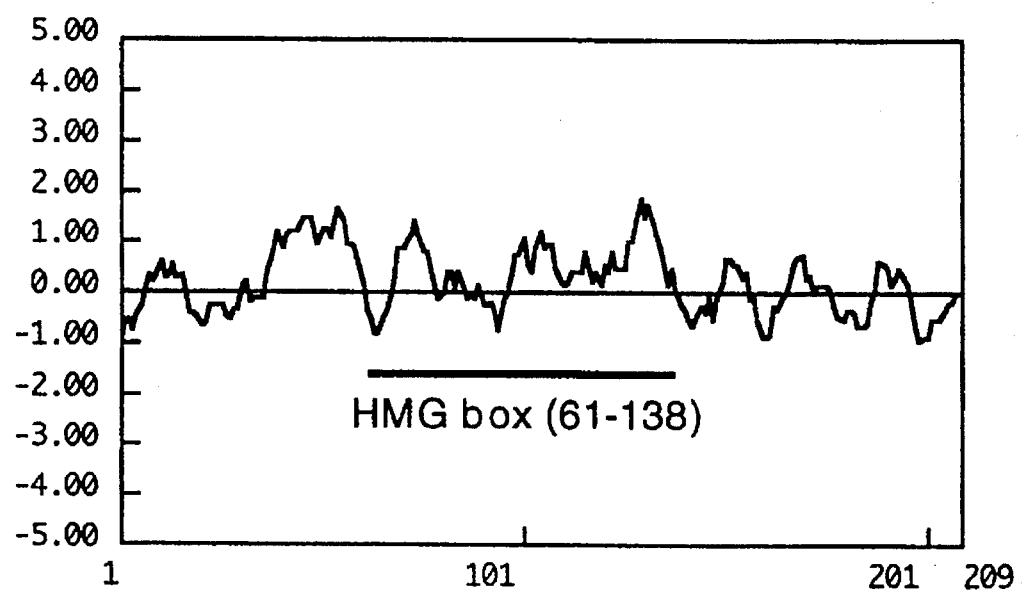
FIG. 5B is the hydropathy profile of porcine SRY open reading frame.

The bovine SRY 1.7 Kb gene sequence, composed of 1.6 Kb HindIII genomic fragment and 3' cDNA sequences, is presented in FIG. 2A. Primers for cloning and sequencing are indicated by underlining, and arrows are used to indicate directionality (sense, →; antisense, ←; FIGS. 2A and 2B). The actual size of the genomic HindIII fragment is 1564 bp, while there are an additional 80 bp of sequence contributed by 3' cDNA to the poly-A tail. The coding SRY sequence based on open reading frames (ORFs) and homology with human and mouse coding sequences is found at the 3' end of the fragment. An analysis of ORFs is presented in FIG. 3A. Possible initiation codons (ATG) are depicted by inverted triangles (∇), and stop codons (TAA, TAG, TGA) are depicted by vertical lines (l), while reading frames 1, 2 and 3 are shown in FIG. 3A. The longest ORF, found in the third reading frame and representing 687 bp of potential coding sequence for the bovine SRY gene, is indicated. A putative start site is identified at nucleotide 912, while a stop site is found at nucleotide 1599. Comparison of translated amino acid sequence between human, mouse, boar and bull is presented in FIG. 4, with the HMG (High Mobility Group) domain delineated. Numbering is based on the porcine sequence in FIG. 4. The depicted SRY sequence is devided into the N-terminal region, the HMG (High Mobility Group) domain, and C-terminal region. Only non-homologous sequences for the HMG domain are shown. Stop codons are represented by the symbol (*) in FIG. 4. Nucleotide and amino acid comparisons in percent homology between human, mouse, boar and bull for the HMG box are shown in Table 2. Outside the HMG box, no notable homology was seen between species. A hydropathy profile of the translated putative bovine SRY protein is presented in FIG. 5A, and for putative porcine SRY protein in FIG. 5S. The method of Hopp TP and Woods KR (1981, PNAS USA, 78:3824–3828) was used with a window frame of 10. The HMG domain, from amino acids 53 to 130 in bovine SRY and 61 to 138 in porcine SRY sequences, is indicated by a solid line in FIG. 5.

TABLE 2

Sequence homology comparisons of HMG box for bovine, human and mouse SRY genes

|  | Bovine | | Porcine | |
| --- | --- | --- | --- | --- |
|  | Nucleotide | Amino Acid | Nucleotide | Amino Acid |
| Human | 83.1% | 76.9% | 83.3% | 83.1% |
| Mouse | 75.4% | 70.5% | 75.7% | 70.1% |
| Pig | 86.0% | 80.5% | — | — |

Figure 6:
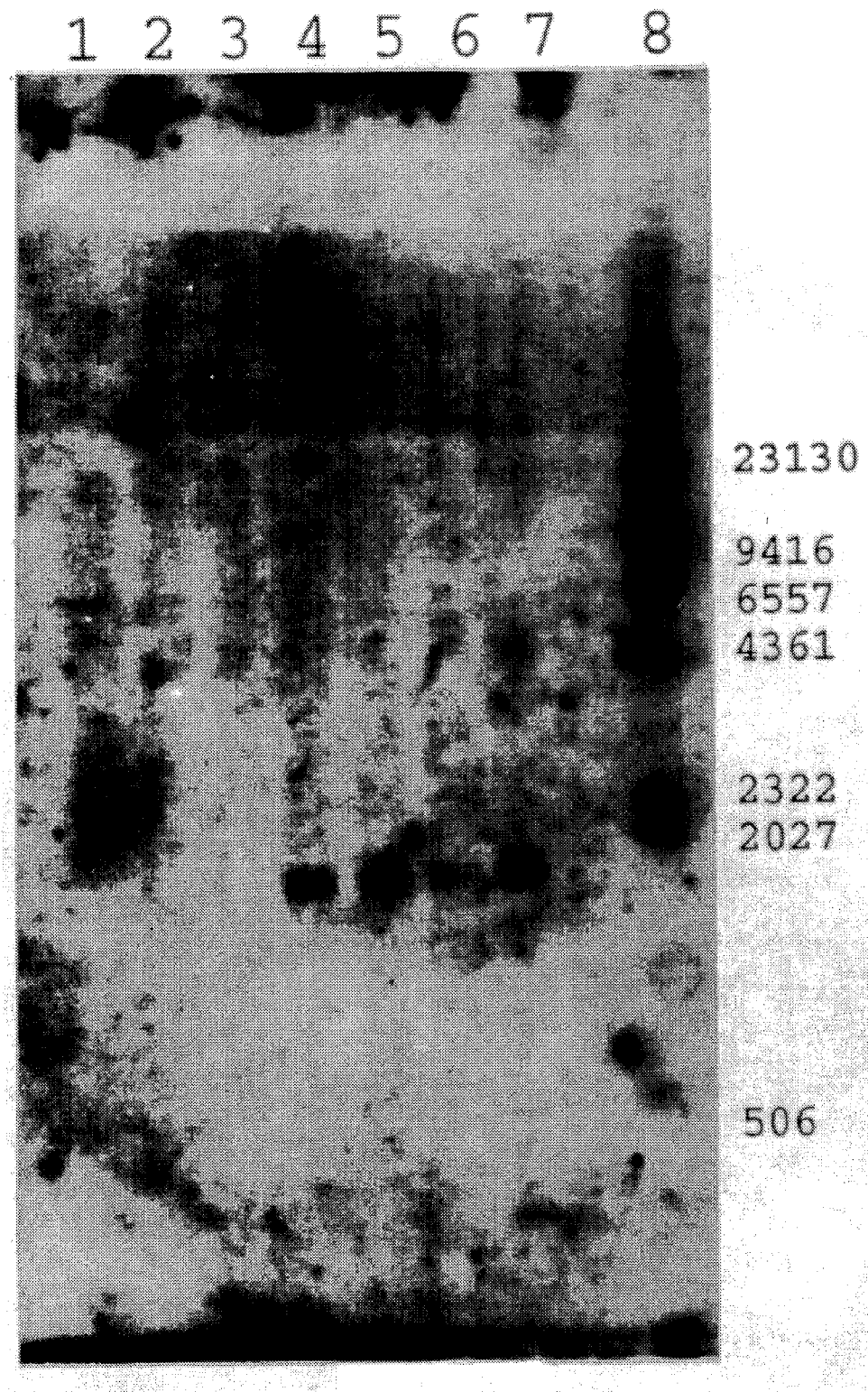
FIG. 6 is a southern analysis of bovine male and female genomic DNA restricted with HindIII.

Southern analysis of bovine male and female HindIII restricted DNA reveals a single band at about 1.6 Kb only in the male samples (FIG. 6). Probe used was digoxigenin labelled G8 fragment. Lanes 1, 2 and 3 represent samples from three different female animals, while lanes 4, 5, 6 and 7 represent samples from four different male animals and lane 8 is a molecular weight standard (Lambda phage digested with HindIII) (FIG. 6). An arrow depicts the band seen at about 1.6 Kb in the male samples.

Southern analysis of porcine male DNA restricted with a variety of enzymes reveals bands at 6 Kb for HindIII and at 1.7 Kb for EcoRI (FIG. 7). The probe used was digoxigenin labelled bovine G8 fragment. Lane 1, BamHI; lane 2, BglII; lane 3, ClaI; lane 4, EcoRI; lane 5, HindIII; lane 6, KpnI; lane 7, PstI; lane 8, Sac I; lane 9, XbaI; and lane 10 is molecular weight standards (Lambda phage digested with HindIII) (FIG. 7).

Figure 8:
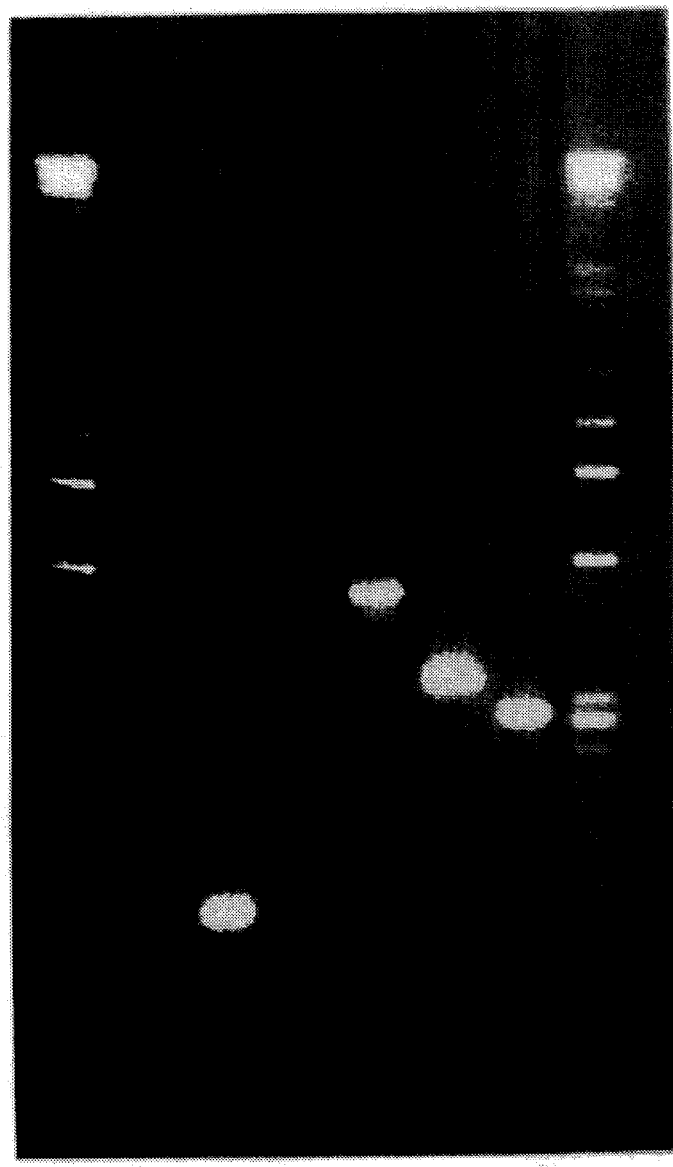
FIG. 8 is a PCR amplification of bovine male and female genomic DNA using bovine male specific oligonucleotide primers.

Results of the PCR analysis of bovine genomic DNA are presented in FIG. 8. No bands of the predicted sizes were seen in the female samples although low molecular weight "primer dimer" banding patterns can be seen in a non-specific fashion in several samples. The male DNA samples showed specific bands of the predicted molecular size.

Presented are 1644 bp of DNA sequences derived from the SRY gene of the bull. This represents the 1.6 Kb HindIII restricted band described by Sinclair et al. (1990, Nature, 346:240–244) and confirmed by Southern analysis (FIG. 6), as well as 3' cDNA sequences derived by RT.PCR cloning. An open reading frame of 687 bp is found at the 3' end of these sequences. The interspecies homology of SRY DNA binding domain (or HMG box) is strong and for 5' and 3' regions of the gene are practically nil. A potential explanation for this lack of sequence conservation between species is the hypothesis that SRY is an important evolutionary player in the process of speciation (Whitfield LS et al., 1993, Nature, 364:713–715).

The specificity of the open reading frame sequences of bovine SRY gene for male bovine DNA is evident from the Southern analysis using three female and four male DNA samples.

Amplification of bovine SRY sequences for genetic sexing of bovine tissues or cells using PCR, LCR and solid phase detection methods are now possible and results are forthcoming.

Also presented are 1667 bp of genomic DNA sequences derived from the SRY genomic region of the pig DNA. This represents the 1.7 Kb EcoRI restriction band depicted in the Southern analysis of boar genomic DNA (FIG. 7).

The present invention will be more readily understood by referring to the following examples which are given to illustrate the invention rather than to limit its scope.

EXAMPLE I

Bovine genetic sex determination

Genetic sex determination in the bovine animal based on SRY gene sequences via analysis of tissue samples includes sexing of embryos.

Knowledge of sex phenotype defining gene sequences can be of use for animal agriculture, particularly as it pertains to sexing of bovine and porcine embryos. The SRY gene sequences of the present invention are particularly attractive to this end as the SRY gene product is the first known male specific gene product involved early in the developmental cascades which differentiate male and female sexual phenotypes.

A description of bovine and porcine SRY gene sequences is a necessary prerequisite in the development of this technology for genetic sexing and sexing of embryos based on SRY sequences. The method for embryo sexing of the present invention is based on genetic amplification of the SRY sequences. For the purposes of the example the bovine species is considered, but the porcine species could be equally considered.

Method A: amplification of SRY sequences from genomic DNA

Embryos at the 2 to 32 cell stages are derived in vitro or collected in vivo. A sample of approximately 2 or more cells is collected via microsurgery either immediately or after further in vitro development. The nuclear DNA is extracted from these cells and is subjected to sequential DNA amplification via PCR in the presence of:

(a) an external pair of primers such as bSRY.A and bSRY.1, designed to amplify between 300 and 400 base pairs of bovine SRY sequences centered around the HMG box of the SRY gene; and (b) an internal pair of primers such as bSRY.B and bSRY.2, designed to amplify between 200 and 300 base pairs of bovine SRY sequences again centered around the HMG box of the SRY and internal to the primers described in (a).

After the second amplification, products are analyzed for the presence of bSRY.B- bSRY.2 fragments via methods of detection such as agarose gel electrophoresis or fluorescent or electrochemiluminescent detection. Presence of SRY sequences in the sample confirms the presence of the SRY gene, the male genotype, and thus the genetic potential to display the male phenotype. Absence of SRY sequences in the sample confirms the female genotype. Amplification of control sequences, not specifically related to sex, confirms the methodology for both male and female embryos.

Method B: amplification of SRY sequences based on detection of RNA

The two cell to bastocyst pre-implantation male embryo is reported to transcribe the SRY gene, and thus SRY sequences can be detected at the level of RNA (Zwigman T. et al., 1993, PNAS USA 90:814–817). Thus embrio sex determination is performed by surgical removal of one or several cells of the pre-implantation embryo. RNA is recovered from these cells and then reverse transcribed to produce cDNA, and PCR amplification of the cDNA is performed using SRY specific primers as described for genomic DNA detection of SRY sequences

EXAMPLE II

Porcine genetic sex determination

Genetic sex determination in the porcine animal based on SRY gene sequences via analysis of tissue samples including sexing of embryos.

Detection of porcine SRY sequences from genomic DNA as well as transcribed RNA are detected from porcine tissue including embryo tissue via methods essentially identical as to those described in Example 1, except that porcine specific SRY primers replace bovine specific SRY primers.

EXAMPLE III

Manipulation of domesticated animals sexual phenotype

Sexual phenotype manipulation in domesticated animals is effected via transgenesis using SRY gene coding, promoter and control sequences. The pig is used herein as an example.

Porcine SRY gene and promoter sequences have been isolated in accordance with the present invention, and can be used to modify sexual phenotype expression in the pig via transgenic manipulations. SRY gene expression is seen naturally in the developing but sexually uncommitted somatic support cells of the genital ridge during embryonic sexual differentiation (i.e. progenitor Sertoli cells). This normal expression of the SRY gene by these cells in genetic male animals initiates the genetic developmental cascade which results in the physical expression of the male phenotype. In contrast, lack of expression of the SRY gene in these cells (as occurs naturally in genetic females which lack the SRY gene sequences), results in the female genetic developmental cascade occurring and the expression of the female phenotype.

Transgenic expression of exogenous gene products in tissue and developmentally specific patterns, as defined by promoter sequences, is a well known procedure in the art of transgenic production (Palmiter R. D. et al., 1987, Cell, 50:435–443). The functional SRY gene promoter is believed to reside within the first 310 bp of sequences 5' to the ATG start site (Su and Lau, 1993, Am. J. Hum. Genet., 52:24–38). SRY gene promoter controlled expression of such transgenes as for example, but not limited to, inactive mutated molecules of the SRY protein, the diphtheria toxin subunit A gene product (Palmiter R. D. et al., 1987, Cell, 50:435–443), the lectin ricin subunit A gene product, the aptosis producing gene products, could result in functional ablation and/or cell death of the expressing cell types. Expression of these ablation transgenes in a tissue targeted, developmentally defined manner via SRY promoter and control sequences in genetically male animals would result in ablation of the SRY gene functions and/or progenitor Sertoli cells, with a subsequent lack of developmental signals for the male phenotype, and by consequence development of the female phenotype.

Furthermore, development of controllable or inducible promoters for transgene expression (Palmiter R. D. et al., 1982, Nature, 300:611–615; Fieck A. et al., 1992, Nucleic Acids Res., 20(17):1785–1791), or transgene function via alpha complementation, or transgene function via recombinase mediated gene activation (O'Gorman S. et al., 1991, Science, 251:1351–1355; Orban R. C. et al., 1992, PNAS USA, 89:6861–6865) would result in a further ability to control transgene expression and function and a further refinement of the art.

These methodologies which depend upon a description of the porcine SRY gene sequences including promoter and control sequences are of considerable interest to the porcine industry where the male phenotype is undesirable due to economic and aesthetic reasons.

Figure 9C:
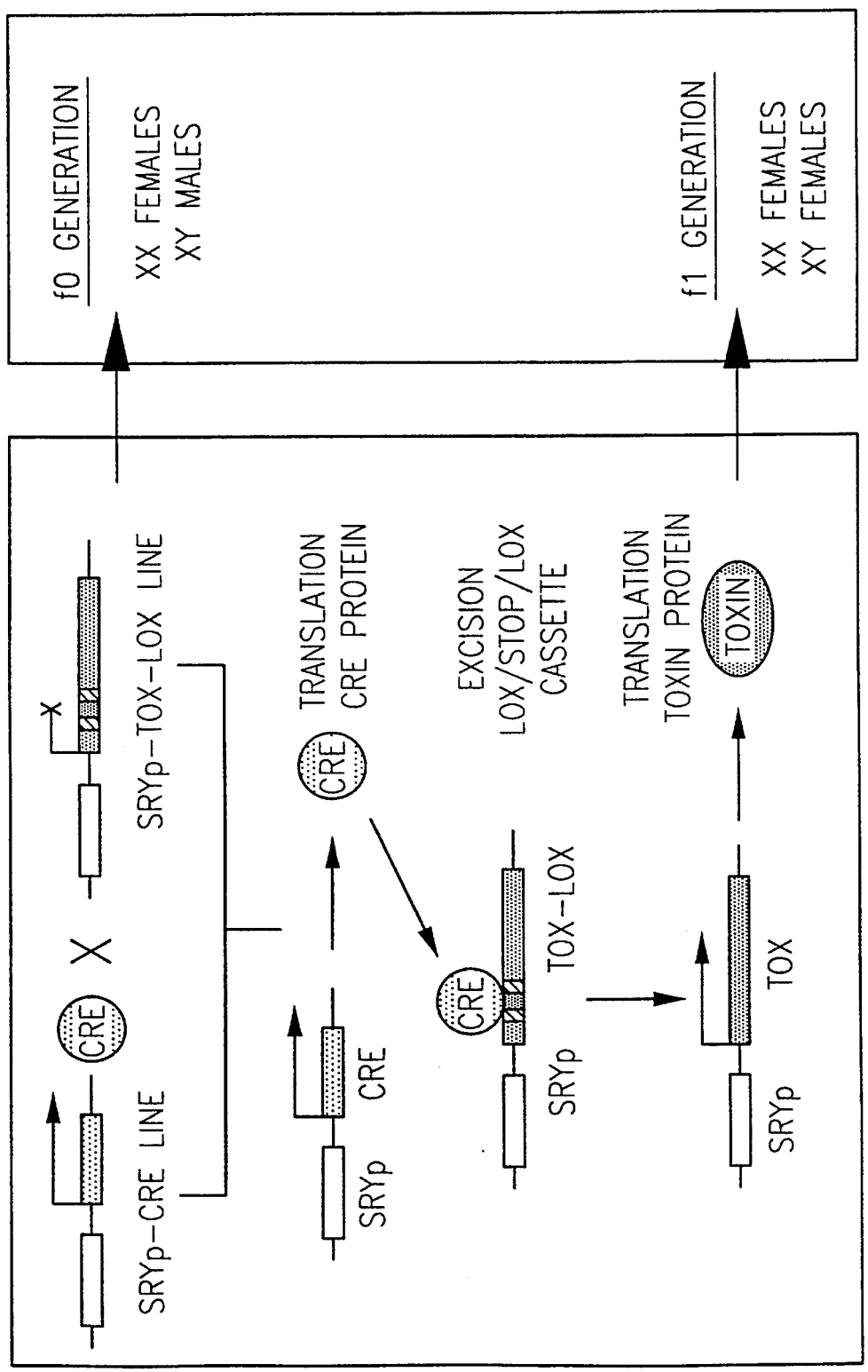
FIG. 9 is a pictoral description of the method of sex phenotype manipulation in transgenic animals via the use of SRY promoter and control sequences.

A pictoral description of the method is presented in FIG. 9. Separate genetic constructs are generated as follows:

a) porcine SRY promoter sequences driving the expression of the bacterial CRE recombinase protein DNA sequences (or other switch encoding DNA sequences), designated SRYp-CRE (FIG. 9A); and b) porcine SRY promoter sequences driving the expression of the diptheria A chain toxin (or other cell ablation encoding) DNA sequences. The diptheria A chain toxin DNA sequences are further modified such that for example immediately downstream of the transcriptional start site, two parallel LOX sequences are inserted with an intervening sequence containing stop codons (ie LOX-STOP-LOX) in all three transcriptional frames as well as a shift in the transcriptional reading frame. This construct is designated SRYp-TOX-LOX (FIG. 9B).

Separate transgenic lines of pigs are generated using conventional transgenic techniques for the SRYp-CRE construct to derive the SRYp-CRE line and the SRYp-TOX-LOX construct to derive the SRYp-TOX-LOX line of animals. The SRYp-CRE line of animals will express the CRE protein under the control of the SRY promoter in the developing but sexually uncommitted gonads in both XX and XY fetuses. The CRE protein by itself will be innocious and these animals will reproduce normally. The SRYp-TOX-LOX line of animals will not express toxin sequences in the developing gonads due to the insertion of the LOX-STOP-LOX cassette into the coding sequences of the toxin gene. These animals will reproduce normally. Both lines of animals are bred to homozygosity for their respective transgenes. Upon mating of the SRYp-CRE line of swine with the SRYp-TOX-LOX line of swine (FIG. 9C), the Cre protein will be again activated in the primordial gonad by the SRY promotor. This time the CRE protein will find its LOX recognition sequences for recombination, and will excise the LOX-STOP-LOX cassette from the SRYp-TOX-LOX transgene. This will repair the TOX sequences and allow the SRY promoter to drive transcription of TOX RNA sequences resulting of production of diptheria toxin A protein (or other ablation promoting products) and cell death of the primordial gonadal cells. This genetic ablation of embryonic gonadal tissue will result in expression of the female phenotype in both XX and XY fetuses.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. An oligonucleotide probe for detection of bovine or porcine male genomic DNA, which comprises the nucleotide sequences selected from the group consisting of SEQ ID NO:1 and SEQ ID NO:2, or fragments thereof which comprise sequences outside of the HMG box, wherein no notable homology is seen between species and whereby, the oligonucleotide probe either exclusively or predominantly hybridizes to sequences outside of said HMG box.

2. An oligonucleotide primer for detection of bovine or porcine male genomic DNA, which comprises a DNA sequence selected from the group consisting of:

GCCGCGAGATGGCCATTCTTCCAGGAGGC SEQ ID NO:3;

GGGAATTCAGATCAGCAAGCAGCTGGGA SEQ ID NO:5;

ACAGTCATAGCGCAAATGATCAGTG SEQ ID NO:6;

GAGAACATGTTAGGGAGAGCAGCCA SEQ ID NO:7;

GGGTTGCATAGTATTGAAGAGTCTGC SEQ ID NO:8;

GAAGCGATTTCTGTGGCCTCTTGG SEQ ID NO:9;

GAATTCAGCCAATGTTACCTTATTGTGGC SEQ ID NO:10;

GATTCAGCTGCTGTGATGCTCT SEQ ID NO:11;

TATGCAATCGATGCATGT SEQ ID NO:12;

ATAGCCCGGGTATTTGTCTC SEQ ID NO:13;
GAATTCTAGTAGTCTCTGTGCCTCC SEQ ID NO:14;
GCGAGAGTAGTTGTGC SEQ ID NO:15;
CTACTCCCCAACCGTCA SEQ ID NO:16;
TCTTCCTTGTGCACAGACAG SEQ ID NO:17;
TTATTGTCGCCCAGGCTTGT SEQ ID NO:18;
CACACTGATCATTTGCGC SEQ ID NO:19;
AGGGTTAGTGATAGCAT SEQ ID NO:20;
AGAAACAAGAATGACGA SEQ ID NO:21;
GTTAGCAGAGCCTCCAG SEQ ID NO:22;
AAGTCACTCACAGCCCA SEQ ID NO:23;
CATGGGTCGCTTGACAC SEQ ID NO:24;
GCTATGCTAAGGATTAT SEQ ID NO:25;
GACAATTCATAGCTCAAACGATGGAC SEQ ID NO:26;
ACTAGAGGAAGTGGTAGAGAGAGTG SEQ ID NO:27;
ACTTGGCTGCATAGTACTGCCGCC SEQ ID NO:28; and
GGAAGCAAATTCTGTGCCCTCTCTC SEQ ID NO:29.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
( A ) LENGTH: 1661 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
( A ) CHROMOSOME/SEGMENT: Y- chromosome, SRY gene ( x i ) SEQUENCE DESCRIPTION: SEQ ID NO:1:

| | | | | | |
|---|---|---|---|---|---|
| AAGCTTTTTT | TTTTGTTTTG | TTCTATTTAG | TTTTGATCAT | CTGTTAGGTA | AAAGTGCAGA | 60 |
| AGAGAGTGAT | AGATATTACT | TCTGCACAGC | CTACGCATCT | AAGACACCAC | ACACCAACCC | 120 |
| CCCCCTCCCA | CTTTTCCTAC | TCCCCAACCG | TCAGAACAAA | AAAATAAAAA | TCAGTCCCTT | 180 |
| TGAAGTGTTA | TATTAACACC | AGGGAACTGC | TTGGGTACCA | AGGTTATGTG | TTTTTTCTTT | 240 |
| TAATGGAACA | GGTTTTTAAT | CTAATTTTAG | TTGTATCTGA | GATTGCCTGT | TAAATATGTG | 300 |
| TTAGTATATA | TTAGCATTCT | GAAAGTCGTT | AGCACAGATA | ATAGAATTAC | CAGTTATTAG | 360 |
| CTACTGGAAT | ACGTACATAG | ATTTTTCAGC | TGCACTTTGA | GCCTAAGTGG | AGAAGCAGGG | 420 |
| TTAGTGATTA | GCATGGATTG | GGTATCTGTG | TATTCAAATA | TATAACAGGA | TTGGGCTGTT | 480 |
| TTTCATCTTT | TTTTGTTTAA | GATAACATTC | TCTTACATTC | ATAACCGTAG | ACAATTTGCT | 540 |
| AGTATGTCTG | CTGCACCTTC | ATCCTTTGAA | ATAAGTATAT | GAAATAACT | TCATAATGAC | 600 |
| ACTTTTTGTA | TTTTTAAGCA | GGTGTTAGCA | CATTCACAAA | TTCTGATTAG | ATGTAAACAA | 660 |
| AGAAGAAAGC | AGAGCCTTAA | TATCCTGTTA | AGTAGCTTTG | CTTGAGAAAG | AGTAGGTTGA | 720 |
| TGGGTTTGGG | CTGACTGCCA | GGACGTATTG | AGGGGAGGTA | TTGGGGGCGG | AGAAATAAAT | 780 |
| ATTTCACTGT | ATATATTGCA | CTAAGTCAGT | CTGTGGTAAG | AACAACTTAT | GAATAGCACC | 840 |
| ATAATTTTTA | GAACGCTTAC | ACCGCATATT | ACTTCCTCCC | CTTTTAAACA | GTGCAGTCGT | 900 |
| ATGCTTCTGC | TATGTTCAGA | GTATTGAACG | ACGATGTTTA | CGATCCAGCT | GTGGTACAGC | 960 |
| AACAAACTAC | TCTCGCTTTT | AGGAAAGACT | CTTCCTTGTG | CACAGACAGT | CATAGCGCAA | 1020 |
| ATGATCAGTG | TGAAAGGGGA | GAACATGTTA | GGGAGAGCAG | CCAGGACCAC | GTCAAGCGAC | 1080 |
| CCATGAACGC | CTTCATTGTG | TGGTCTCGTG | AACGAAGACG | AAAGGTGGCT | CTAGAGAATC | 1140 |
| CCAAAATGAA | AAACTCAGAC | ATCAGCAAGC | AGCTGGGATA | TGAGTGGAAA | AGGCTTACAG | 1200 |
| ATGCTGAAAA | GCGCCCATTC | TTTGAGGAGG | CACAGAGACT | ACTAGCCATA | CACCGAGACA | 1260 |
| AATACCCGGG | CTATAAATAT | CGACCTCGTC | GGAGAGCCAA | GAGGCCACAG | AAATCGCTTC | 1320 |
| CTGCAGACTC | TTCAATACTA | TGCAACCCGA | TGCATGTAGA | GACATTGCAC | CCCTTCACAT | 1380 |
| ACAGGGATGG | TTGTGCCAAG | ACCACATACT | CACAAATGGA | AAGCCAATTA | GCCGGTCAC | 1440 |
| AGTCCGTGAT | CATAACCAAT | TCACTCCTGC | AAAAGGAGCA | TCACAGCAGC | TGGACAAGCC | 1500 |
| TGGGCCACAA | TAAGGTAACA | TTGGCTACAC | GGATTTCGGC | GGACTTTCCC | TGTAACAAAA | 1560 |
| GCTTAGAGCC | TGGACTTTCT | TGTGCTTATT | TTCAATATTG | ACTTCCTTAC | TCTCGCTAAC | 1620 |

AAAGGCGCTC TTTATCTCAA TTTTAAAAAA AAAAAAAAAA A  1661

( 2 ) INFORMATION FOR SEQ ID NO:2:

( i ) SEQUENCE CHARACTERISTICS:
        ( A ) LENGTH: 1667 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
        ( A ) CHROMOSOME/SEGMENT: Y- chromosome, SRY gene ( x i ) SEQUENCE DESCRIPTION: SEQ ID NO:2:

| | | | | | | |
|---|---|---|---|---|---|---|
| GAATTCCCAA | TTATTTGCCC | ACAGGAAAAC | TTAACAGAAT | TTTCAATAGT | TCTTTAAGTA | 60 |
| GAAGTGAAGA | AACAAGAATG | ACGACTAGCA | TTCAACTCTA | TAACATCCGC | CGCCTGGCAG | 120 |
| GCCACGTGCC | TGCATTCTTG | CCTGTGGGCC | TGAGTGCTCT | AATGGCCGAA | AGGAAAGGAA | 180 |
| TTGGGTTATC | TTGAATCTCT | GTGTTAAACA | TAGCATTTAC | ATATGCTCAT | AACGATAAAC | 240 |
| CATTGTCAGA | TGCTGCTGCA | CCGTCATCCT | TTAATTGAG | TGGATAAAAT | AAAATAACTT | 300 |
| AATAATGACA | AAGTTTCCGG | TTTTTAAGG | TTAGCAGAGC | CTCCAGCAAC | TCGGATTAGA | 360 |
| CCTAGAACAG | AAAGCAAGCC | TTATTATCAT | AATAAGTAAG | CAGTTTTGCT | TGAGAATGGG | 420 |
| TAGGTTGGTT | GGTTCGGCTT | TGGCTGGCTG | GCTGCCTGCC | GATCGCAGCG | GTTTCCAGGG | 480 |
| GAGGTACTGG | GGGCGGAGAA | ATTGGTATTT | CACTACAAAG | ATTAGAGTTA | CTCAAATCTC | 540 |
| TGGTGGAAAT | AACCTTTAAA | TAGTGAAGAC | AACTTTCCAA | ACGTTACGCT | TTTGATTTCG | 600 |
| CTTCCTCCCC | CTTTTCAAAT | GGTGCAGTCA | TATGCTTCTG | CTATGTTCAG | AGTATTGAAA | 660 |
| GCGGACGATT | ACAGCCCAGC | GGCACAGCAG | CAAAATATTC | TCGCCTTGGG | GAAAGGCTCC | 720 |
| TCACTATTTC | CGACGGACAA | TCATAGCTCA | AACGATGGAC | GTGAAACTAG | AGGAAGTGGT | 780 |
| AGAGAGAGTG | GCCAGGATCG | TGTCAAGCGA | CCCATGAACG | CTTTCATTGT | GTGGTCTCGT | 840 |
| GATCAAAGGA | GAAAAGTGGC | TCTAGAGAAC | CCTCAAATGC | AAAACTCAGA | GATCAGCAAG | 900 |
| TGGCTGGGAT | GCAAGTGGAA | AATGCTTACA | GAAGCCGAAA | AGCGCCCATT | CTTCGAGGAG | 960 |
| GCACAGAGGC | TACAGGCGGT | GCACCGAGAT | AAATACCCGG | CTATAAATA | CCGACCTCGT | 1020 |
| CGCAAGGGAG | AGAGGGCACA | GAATTTGCTT | CCGGCAGAGG | CGGCAGTACT | ATGCAGCCAA | 1080 |
| GTGCGCGTAG | AGGAGAGGAT | GTATCCCTTC | ACATACACAG | TCGCCAAGGC | CAAGTGCTCA | 1140 |
| GGAACAGAAA | GCCAGTTAAG | TCACTCACAG | CCCATGAACA | TAACCAGCTC | ACTTCTGCAA | 1200 |
| CAGGAGGATC | GCTGCAACTG | GACAGGCCTG | TGCACAGTAG | GGTAACATCC | ACCGGGCAGA | 1260 |
| TCCGCGCCGA | CTTGCCTTTT | CACCGTGGTT | TACAGCCGGG | ACTTTCTCAC | ATTTATTTTC | 1320 |
| CATATTGATT | TCCTTTACTG | TCGCGAACAG | AGGGCCTATT | CATCTCAGTT | TTACTGTTAT | 1380 |
| TTCACCTGTG | ACTTAGTTTC | AGATTAAGGC | AGATTAACAT | GTTTGACCTA | TAAAGAATTA | 1440 |
| GGGCATGCCA | ATATGACTCA | ACCTGTCTTT | ACGACTGCTT | AAAAGAGCAC | TACCTTAATA | 1500 |
| AGAAAGTATC | TTAACACACA | AACTGCTTGA | TTTCGAAAAC | CATCTGTTTT | TCCTTCTAAT | 1560 |
| AGAACAATTT | TTTTATACCT | AATTTTAGTT | GTTCCCGTGA | TTAGCCATTA | AGTACGTAAC | 1620 |
| AGTATATATT | AGTATTCTGA | TAATCCTTAG | CATAGCTGAT | AGAATTC. | | 1667 |

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
        ( A ) CHROMOSOME/SEGMENT: Y- chromosome, SRY gene ( x i ) SEQUENCE DESCRIPTION: SEQ ID NO:3:

GCCGCGAGAT GGCCATTCTT CCAGGAGGC    29

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
        ( A ) CHROMOSOME/SEGMENT: Y- chromosome, SRY gene ( x i ) SEQUENCE DESCRIPTION: SEQ ID NO:4:

GGGAATTCAT GCACAGAGAG AAATACCC    28

( 2 ) INFORMATION FOR SEQ ID NO:5:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
        ( A ) CHROMOSOME/SEGMENT: Y- chromosome, SRY gene ( x i ) SEQUENCE DESCRIPTION: SEQ ID NO:5:

GGGAATTCAG ATCAGCAAGC AGCTGGGA    28

( 2 ) INFORMATION FOR SEQ ID NO:6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO (v i i i) POSITION IN GENOME:
            (A) CHROMOSOME/SEGMENT: Y- chromosome, SRY gene (x i) SEQUENCE DESCRIPTION: SEQ ID NO:6:

ACAGTCATAG CGCAAATGAT CAGTG                                                                25

(2) INFORMATION FOR SEQ ID NO:7:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (i i) MOLECULE TYPE: DNA (genomic)

(i i i) HYPOTHETICAL: NO (i v) ANTI-SENSE: NO (v i i i) POSITION IN GENOME:
            (A) CHROMOSOME/SEGMENT: Y- chromosome, SRY gene (x i) SEQUENCE DESCRIPTION: SEQ ID NO:7:

GAGAACATGT TAGGGAGAGC AGCCA                                                                25

(2) INFORMATION FOR SEQ ID NO:8:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (i i) MOLECULE TYPE: DNA (genomic)

(i i i) HYPOTHETICAL: NO (i v) ANTI-SENSE: NO (v i i i) POSITION IN GENOME:
            (A) CHROMOSOME/SEGMENT: Y- chromosome, SRY gene (x i) SEQUENCE DESCRIPTION: SEQ ID NO:8:

GGGTTGCATA GTATTGAAGA GTCTGC                                                               26

(2) INFORMATION FOR SEQ ID NO:9:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (i i) MOLECULE TYPE: DNA (genomic)

(i i i) HYPOTHETICAL: NO (i v) ANTI-SENSE: NO (v i i i) POSITION IN GENOME:
            (A) CHROMOSOME/SEGMENT: Y- chromosome, SRY gene (x i) SEQUENCE DESCRIPTION: SEQ ID NO:9:

GAAGCGATTT CTGTGGCCTC TTGG                                                                 24

(2) INFORMATION FOR SEQ ID NO:10:

(i) SEQUENCE CHARACTERISTICS:
            (A) LENGTH: 29 base pairs
            (B) TYPE: nucleic acid
            (C) STRANDEDNESS: single (D) TOPOLOGY: linear (ii) MOLECULE TYPE: DNA (genomic)

(iii) HYPOTHETICAL: NO (iv) ANTI-SENSE: NO (viii) POSITION IN GENOME:
    (A) CHROMOSOME/SEGMENT: Y- chromosome, SRY gene (xi) SEQUENCE DESCRIPTION: SEQ ID NO:10:

GAATTCAGCC AATGTTACCT TATTGTGGC         29

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (viii) POSITION IN GENOME:
        (A) CHROMOSOME/SEGMENT: Y- chromosome, SRY gene (xi) SEQUENCE DESCRIPTION: SEQ ID NO:11:

GAATTCAGCT GCTGTGATGC TCT         23

(2) INFORMATION FOR SEQ ID NO:12:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (viii) POSITION IN GENOME:
        (A) CHROMOSOME/SEGMENT: Y- chromosome, SRY gene (xi) SEQUENCE DESCRIPTION: SEQ ID NO:12:

TATGCAATCG ATGCATGT         18

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (viii) POSITION IN GENOME:
        (A) CHROMOSOME/SEGMENT: Y- chromosome, SRY gene (xi) SEQUENCE DESCRIPTION: SEQ ID NO:13:

ATAGCCCGGG TATTTGTCTC         20

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
        ( A ) CHROMOSOME/SEGMENT: Y- chromosome, SRY gene ( x i ) SEQUENCE DESCRIPTION: SEQ ID NO:14:

GAATTCTAGT AGTCTCTGTG CCTCC                         25

( 2 ) INFORMATION FOR SEQ ID NO:15:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
        ( A ) CHROMOSOME/SEGMENT: Y- chromosome, SRY gene ( x i ) SEQUENCE DESCRIPTION: SEQ ID NO:15:

GCGAGAGTAG TTGTGC                                  16

( 2 ) INFORMATION FOR SEQ ID NO:16:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
        ( A ) CHROMOSOME/SEGMENT: Y- chromosome, SRY gene ( x i ) SEQUENCE DESCRIPTION: SEQ ID NO:16:

CTACTCCCCA ACCGTCA                                17

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
  ( A ) CHROMOSOME/SEGMENT: Y- chromosome, SRY gene ( x i ) SEQUENCE DESCRIPTION: SEQ ID NO:17:

TCTTCCTTGT GCACAGACAG                                   20

( 2 ) INFORMATION FOR SEQ ID NO:18:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
    ( A ) CHROMOSOME/SEGMENT: Y- chromosome, SRY gene ( x i ) SEQUENCE DESCRIPTION: SEQ ID NO:18:

TTATTGTGGC CCAGGCTTGT                                   20

( 2 ) INFORMATION FOR SEQ ID NO:19:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
    ( A ) CHROMOSOME/SEGMENT: Y- chromosome, SRY gene ( x i ) SEQUENCE DESCRIPTION: SEQ ID NO:19:

CACACTGATC ATTTGCGC                                     18

( 2 ) INFORMATION FOR SEQ ID NO:20:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
    ( A ) CHROMOSOME/SEGMENT: Y- chromosome, SRY gene ( x i ) SEQUENCE DESCRIPTION: SEQ ID NO:20:

AGGGTTAGTG ATTAGCAT                                     18

( 2 ) INFORMATION FOR SEQ ID NO:21:

( i ) SEQUENCE CHARACTERISTICS:
    ( A ) LENGTH: 17 base pairs ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
            ( A ) CHROMOSOME/SEGMENT: Y- chromosome, SRY gene ( x i ) SEQUENCE DESCRIPTION: SEQ ID NO:21:

AGAAACAAGA ATGACGA 17

( 2 ) INFORMATION FOR SEQ ID NO:22:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
            ( A ) CHROMOSOME/SEGMENT: Y- chromosome, SRY gene ( x i ) SEQUENCE DESCRIPTION: SEQ ID NO:22:

GTTAGCAGAG CCTCCAG 17

( 2 ) INFORMATION FOR SEQ ID NO:23:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
            ( A ) CHROMOSOME/SEGMENT: Y- chromosome, SRY gene ( x i ) SEQUENCE DESCRIPTION: SEQ ID NO:23:

AAGTCACTCA CAGCCCA 17

( 2 ) INFORMATION FOR SEQ ID NO:24:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
            ( A ) CHROMOSOME/SEGMENT: Y- chromosome, SRY gene ( x i ) SEQUENCE DESCRIPTION: SEQ ID NO:24:

CATGGGTCGC TTGACAC                                                                       17

( 2 ) INFORMATION FOR SEQ ID NO:25:

( i ) SEQUENCE CHARACTERISTICS:
           ( A ) LENGTH: 17 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
           ( A ) CHROMOSOME/SEGMENT: Y- chromosome, SRY gene ( x i ) SEQUENCE DESCRIPTION: SEQ ID NO:25:

GCTATGCTAA GGATTAT                                                                       17

( 2 ) INFORMATION FOR SEQ ID NO:26:

( i ) SEQUENCE CHARACTERISTICS:
           ( A ) LENGTH: 26 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
           ( A ) CHROMOSOME/SEGMENT: Y- chromosome, SRY gene ( x i ) SEQUENCE DESCRIPTION: SEQ ID NO:26:

GACAATTCAT AGCTCAAACG ATGGAC                                                             26

( 2 ) INFORMATION FOR SEQ ID NO:27:

( i ) SEQUENCE CHARACTERISTICS:
           ( A ) LENGTH: 25 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( v i i i ) POSITION IN GENOME:
           ( A ) CHROMOSOME/SEGMENT: Y- chromosome, SRY gene ( x i ) SEQUENCE DESCRIPTION: SEQ ID NO:27:

ACTAGAGGAA GTGGTAGAGA GAGTG                                                              25

( 2 ) INFORMATION FOR SEQ ID NO:28:

( i ) SEQUENCE CHARACTERISTICS:
           ( A ) LENGTH: 24 base pairs
           ( B ) TYPE: nucleic acid
           ( C ) STRANDEDNESS: single
           ( D ) TOPOLOGY: linear ( i i ) MOLECULE TYPE: DNA (genomic)

(i i i) HYPOTHETICAL: NO (i v) ANTI-SENSE: NO (v i i i) POSITION IN GENOME:
    (A) CHROMOSOME/SEGMENT: Y- chromosome, SRY gene (x i) SEQUENCE DESCRIPTION: SEQ ID NO:28:

ACTTGGCTGC ATAGTACTGC CGCC      24

(2) INFORMATION FOR SEQ ID NO:29:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (v i i i) POSITION IN GENOME:
    (A) CHROMOSOME/SEGMENT: Y- chromosome, SRY gene (x i) SEQUENCE DESCRIPTION: SEQ ID NO:29:

GGAAGCAAAT TCTGTGCCCT CTCTC      25

(2) INFORMATION FOR SEQ ID NO:30:

(i) SEQUENCE CHARACTERISTICS:
    (A) LENGTH: 17 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (v i i i) POSITION IN GENOME:
    (A) CHROMOSOME/SEGMENT: Y- chromosome, SRY gene (x i) SEQUENCE DESCRIPTION: SEQ ID NO:30:

ATTAACCCTC ACTAAAG      17

(2) INFORMATION FOR SEQ ID NO:31:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i v) ANTI-SENSE: NO (v i i i) POSITION IN GENOME:
    (A) CHROMOSOME/SEGMENT: Y- chromosome, SRY gene (x i) SEQUENCE DESCRIPTION: SEQ ID NO:31:

TAATACGACT CACTATAGGG      20

(2) INFORMATION FOR SEQ ID NO:32:

(i) SEQUENCE CHARACTERISTICS:
  (A) LENGTH: 23 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (viii) POSITION IN GENOME:
  (A) CHROMOSOME/SEGMENT: Y- chromosome, SRY gene (xi) SEQUENCE DESCRIPTION: SEQ ID NO:32:

TGGGTAACGC CAGGGTTTTC CCA     23

(2) INFORMATION FOR SEQ ID NO:33:

(i) SEQUENCE CHARACTERISTICS:
  (A) LENGTH: 36 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (viii) POSITION IN GENOME:
  (A) CHROMOSOME/SEGMENT: Y- chromosome, SRY gene (xi) SEQUENCE DESCRIPTION: SEQ ID NO:33:

GAAGCTTGGA TCCGAATTCT TTTTTTTTT TTTTTT     36

(2) INFORMATION FOR SEQ ID NO:34:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (viii) POSITION IN GENOME:
  (A) CHROMOSOME/SEGMENT: Y- chromosome, SRY gene (xi) SEQUENCE DESCRIPTION: SEQ ID NO:34:

GAAGCTTGGA TCCGAATTC     19